US011597980B2

(12) United States Patent
Molyneux et al.

(10) Patent No.: US 11,597,980 B2
(45) Date of Patent: Mar. 7, 2023

(54) SYSTEM AND METHOD FOR DETECTING PATHOGENS IN AN ENVIRONMENT VIA AN ELECTROSTATIC AIR SAMPLER

(71) Applicant: Poppy Health, Inc., Mountain View, CA (US)

(72) Inventors: Sam D. Molyneux, Mountain View, CA (US); Elizabeth Caley, Mountain View, CA (US); Daniela Bezdan, Mountain View, CA (US); Ricardo Vidal, Mountain View, CA (US); Nathan Volman, Mountain View, CA (US); Tae Joon Yi, Mountain View, TX (US)

(73) Assignee: Poppy Health, Inc., Mountain View, CA (US)

( * ) Notice: Subject to any disclaimer, the term of this patent is extended or adjusted under 35 U.S.C. 154(b) by 0 days.

(21) Appl. No.: 17/709,213

(22) Filed: Mar. 30, 2022

(65) Prior Publication Data

US 2023/0011524 A1 Jan. 12, 2023

Related U.S. Application Data

(60) Provisional application No. 63/219,750, filed on Jul. 8, 2021.

(51) Int. Cl.
*C12Q 1/6888* (2018.01)
*B01L 3/00* (2006.01)
(Continued)

(52) U.S. Cl.
CPC ...... *C12Q 1/6888* (2013.01); *B01L 3/502715* (2013.01); *B01L 3/502761* (2013.01);
(Continued)

(58) Field of Classification Search
CPC ................ C12Q 1/6888; C12Q 1/6844; B01L 3/502715; B01L 3/502761; B01L 2200/04;
(Continued)

(56) References Cited

U.S. PATENT DOCUMENTS 7,578,973 B2 8/2009 Call et al.
7,633,606 B2 12/2009 Northrup et al.
(Continued)

FOREIGN PATENT DOCUMENTS

CN 111662816 A 9/2020
CN 112014528 * 12/2020
(Continued)

OTHER PUBLICATIONS

International Search Report and Written Opinion for International Patent Application No. PCT/US2021/64875 dated Mar. 29, 2022; 13 pages.
(Continued)

*Primary Examiner* — Benjamin R Whatley
*Assistant Examiner* — Jacqueline Brazin
(74) *Attorney, Agent, or Firm* — Run8 Patent Group, LLC; Peter Miller; Leah Raddatz

(57) ABSTRACT

One variation of a pathogen detection system includes an air sampler and a cartridge. The air sampler includes: a housing defining an inlet and an outlet; a tunnel arranged within the housing and extending between the inlet and the outlet; a charge electrode arranged within the tunnel proximal the inlet; a cartridge receptacle arranged proximal the outlet and comprising a cartridge terminal; and a power supply configured to drive a voltage between the charge electrode and the cartridge terminal. The cartridge includes: a substrate; a collector plate arranged on the substrate and configured to collect charged bioaerosols moving through the tunnel; and
(Continued)

a connector configured to transiently engage the cartridge receptacle to locate the substrate and the collector plate within the tunnel and electrically couple the collector plate to the cartridge terminal.

20 Claims, 11 Drawing Sheets

(51) Int. Cl.

| | |
|---|---|
| ***C12Q 1/6844*** | (2018.01) |
| ***G01N 1/22*** | (2006.01) |
| ***G01N 21/77*** | (2006.01) |

(52) U.S. Cl.

CPC ......... *C12Q 1/6844* (2013.01); *G01N 1/2273* (2013.01); *B01L 2200/04* (2013.01); *B01L 2300/0645* (2013.01); *B01L 2300/0654* (2013.01); *G01N 2021/7786* (2013.01)

(58) Field of Classification Search

CPC ..... B01L 2300/0645; B01L 2300/0654; G01N 1/2273; G01N 2021/7786

USPC ........................................................ 435/287.2

See application file for complete search history.

(56) References Cited

U.S. PATENT DOCUMENTS

| | | | | |
|---|---|---|---|---|
| 8,272,280 | B2 | 9/2012 | Jones, Jr. | |
| 8,539,840 | B2 | 9/2013 | Ariessohn et al. | |
| 8,578,796 | B2 | 11/2013 | Cho | |
| 8,689,648 | B1 | 4/2014 | Heff | |
| 9,689,792 | B1 | 6/2017 | Sickenberger et al. | |
| 10,919,047 | B2 | 2/2021 | Mainelis et al. | |
| 11,300,484 | B1 | 4/2022 | Bango | |
| 11,366,116 | B1 * | 6/2022 | Meagher .............. | G01N 33/548 |
| 2007/0116607 | A1 * | 5/2007 | Wang ................ | B01L 3/502715 422/83 |
| 2008/0014576 | A1 * | 1/2008 | Jovanovich ........... | B01L 3/5027 422/50 |
| 2008/0281528 | A1 * | 11/2008 | Relle, Jr. .............. | G01N 1/2273 702/50 |
| 2011/0251084 | A1 | 10/2011 | Brenan et al. | |
| 2011/0252897 | A1 | 10/2011 | Swenson et al. | |
| 2012/0174650 | A1 | 7/2012 | Ariessohn et al. | |
| 2013/0045496 | A1 * | 2/2013 | Jansen ............. | G01N 35/00029 435/8 |
| 2016/0362730 | A1 | 12/2016 | Alexander et al. | |
| 2018/0155771 | A1 | 6/2018 | Takahashi et al. | |
| 2019/0025299 | A1 | 1/2019 | Vigneault et al. | |
| 2019/0039076 | A1 * | 2/2019 | Mainelis ................... | B03C 3/47 |
| 2021/0208062 | A1 | 7/2021 | Linden | |
| 2021/0324485 | A1 | 10/2021 | Hodges et al. | |
| 2022/0034763 | A1 | 2/2022 | Dutta | |
| 2022/0091010 | A1 | 3/2022 | Wystup et al. | |
| 2022/0196268 | A1 * | 6/2022 | Goel ......................... | F24F 8/22 |

FOREIGN PATENT DOCUMENTS

| | | | | | |
|---|---|---|---|---|---|
| CN | 112014528 | A | | 12/2020 | |
| JP | 2017096727 | A | | 6/2017 | |
| KR | 20110097199 | | * | 8/2011 | |
| KR | 20110097199 | A | | 8/2011 | |
| WO | 2019018559 | A1 | | 1/2019 | |
| WO | WO-2019018559 | A1 | * | 1/2019 | ............ C12M 1/261 |
| WO | 2019046347 | A9 | | 7/2019 | |
| WO | 2022047340 | A1 | | 3/2022 | |
| WO | 2022081543 | A1 | | 4/2022 | |

OTHER PUBLICATIONS

M. Z. Bazant, J. W. Bush, A guideline to limit indoor airborne transmission of covid-19. Proceedings of the National Academy of Sciences. 118 (2021), doi:10.1073/pnas.2018995118.

Non-Final Office Action for U.S. Appl. No. 17/559,257 dated Jun. 8, 2022; 7 pages.

International Search Report and Written Opinion for International Patent Application PCT/US2022/026201 dated Oct. 5, 2022; 14 pages.

* cited by examiner

SYSTEM AND METHOD FOR DETECTING PATHOGENS IN AN ENVIRONMENT VIA AN ELECTROSTATIC AIR SAMPLER

CROSS-REFERENCE TO RELATED APPLICATIONS

This Application claims the benefit of U.S. Provisional Application 63/219,750, filed on 8 Jul. 2021, which is incorporated in its entirety by this reference.

TECHNICAL FIELD

This invention relates generally to the field of metagenomics and more specifically to a new and useful system for pathogen detection in the field of metagenomics.

DESCRIPTION OF THE EMBODIMENTS

The following description of embodiments of the invention is not intended to limit the invention to these embodiments but rather to enable a person skilled in the art to make and use this invention. Variations, configurations, implementations, example implementations, and examples described herein are optional and are not exclusive to the variations, configurations, implementations, example implementations, and examples they describe. The invention described herein can include any and all permutations of these variations, configurations, implementations, example implementations, and examples.

1. Pathogen Detection System

Figure 1A:
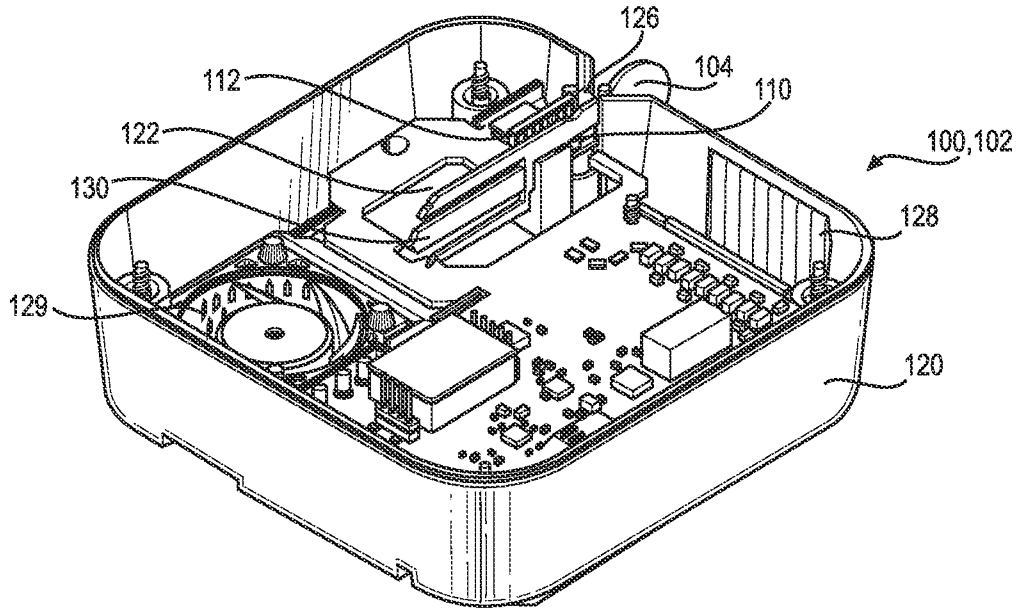
FIGS. 1A and 1B are schematic representations of a system.
Figure 1B:
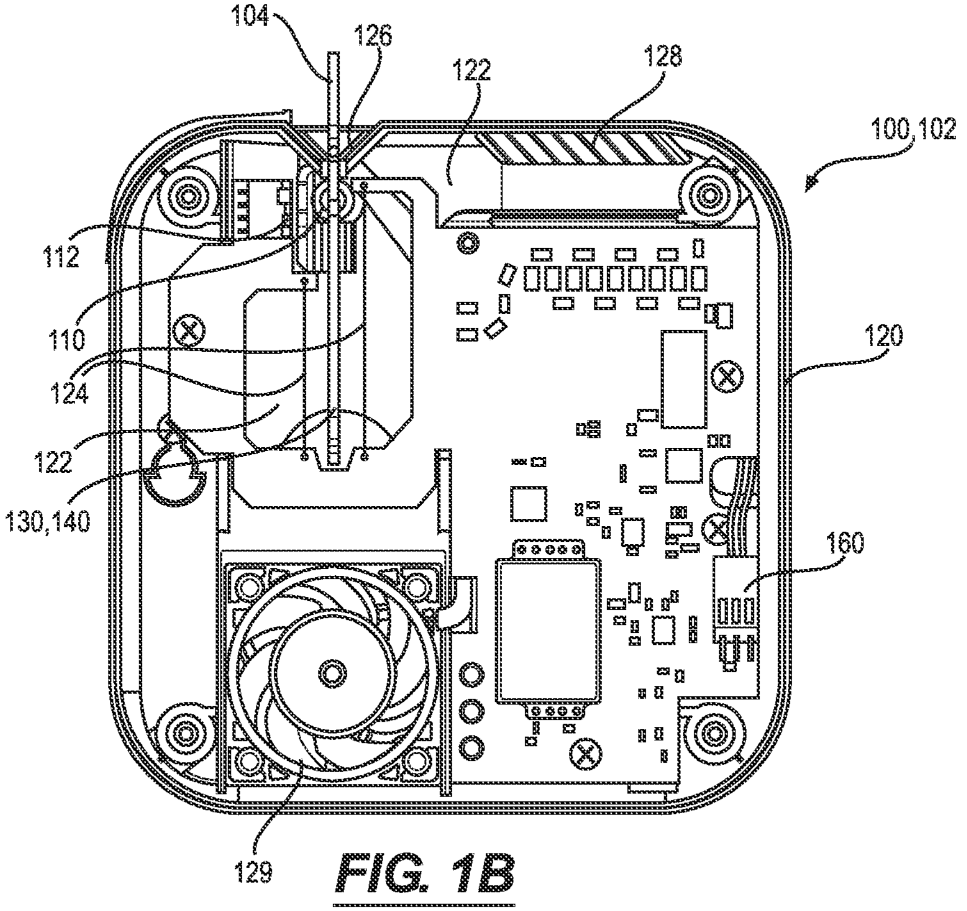
Figure 2A:
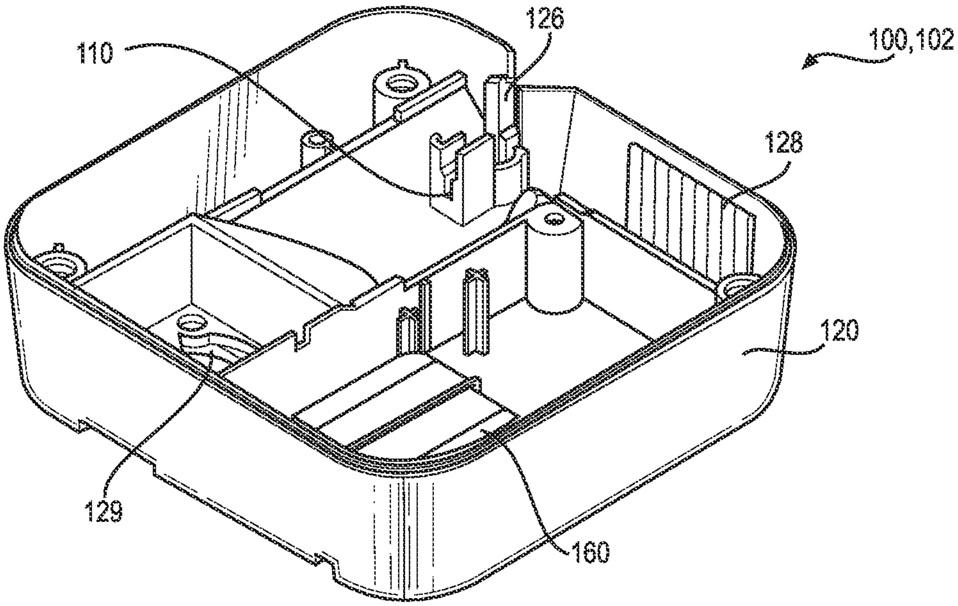
FIGS. 2A and 2B are schematic representations of the system.
Figure 2B:
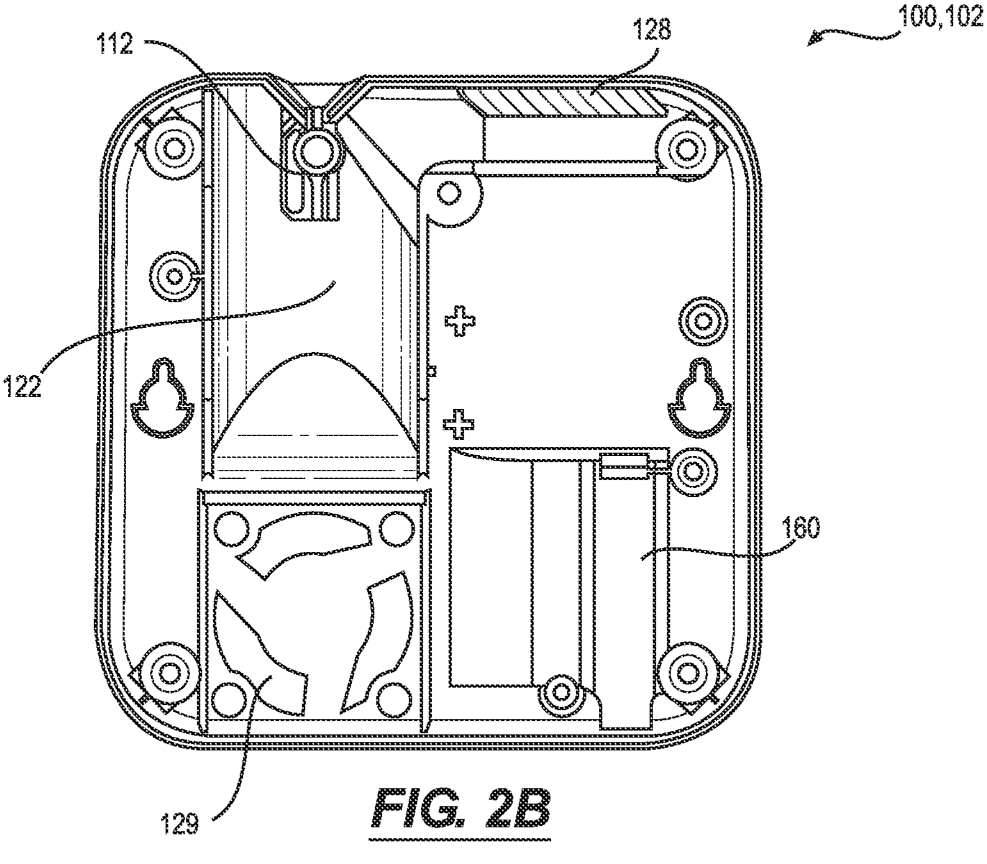
Figure 3:
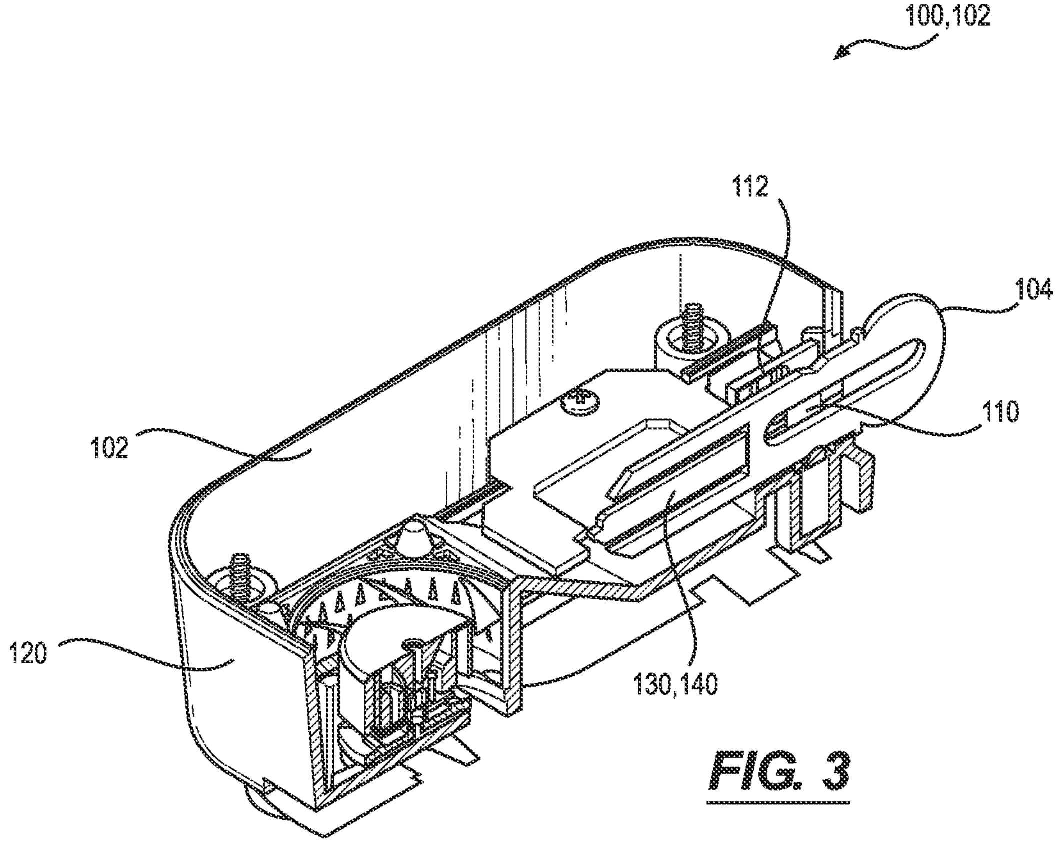
FIG. 3 is a schematic representation of the system.
Figure 4A:
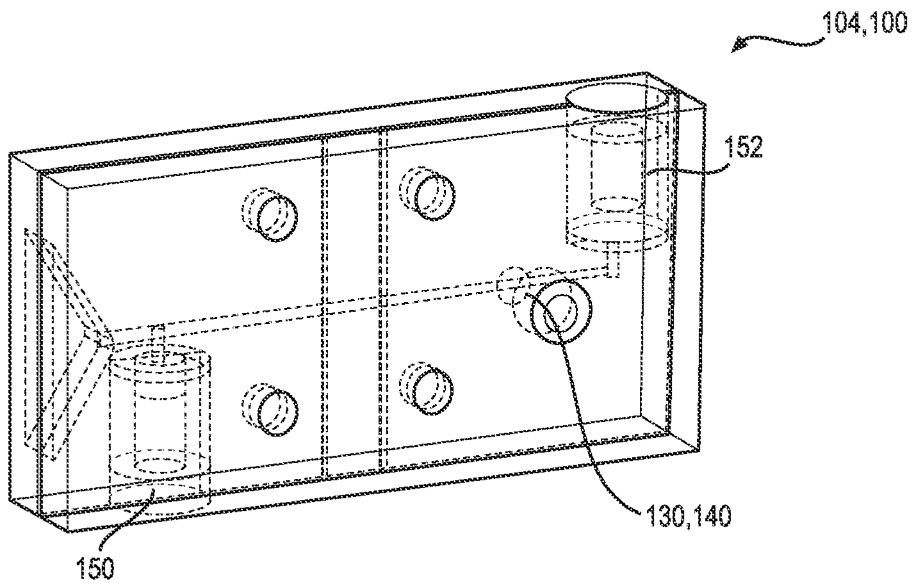
FIGS. 4A and 4B are schematic representations of the system.
Figure 4B:
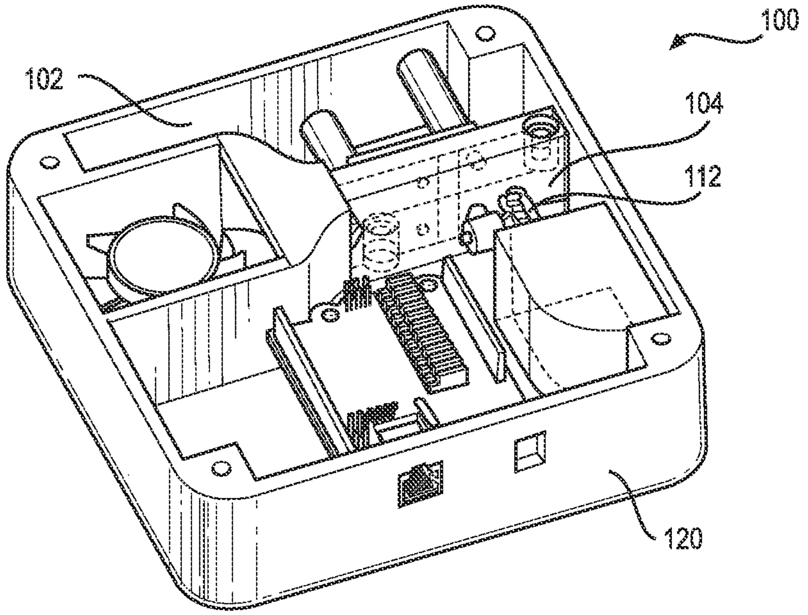
Figure 5A:
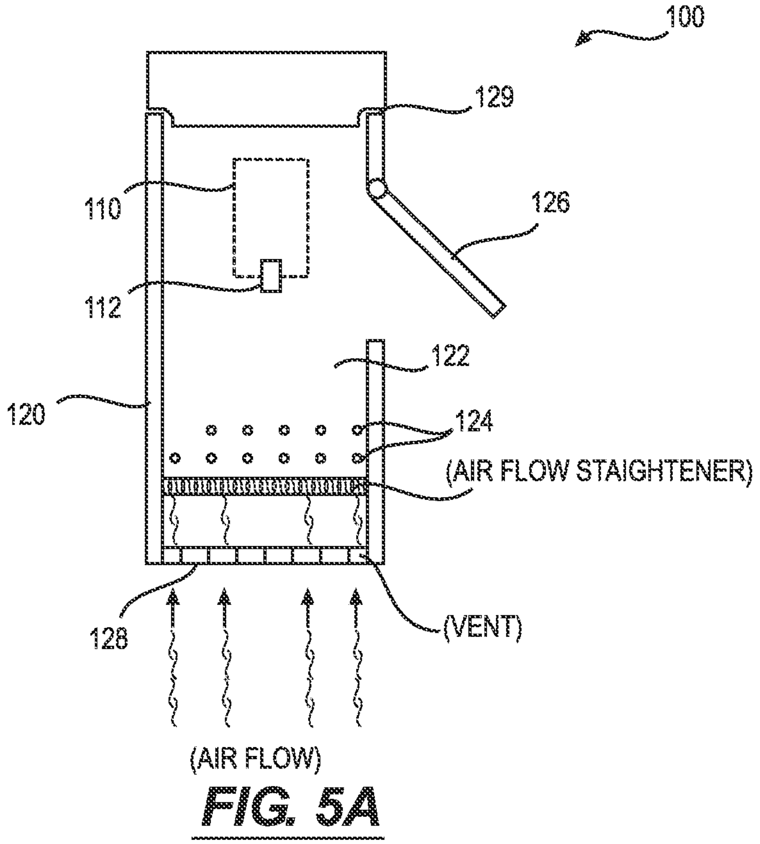
FIGS. 5A and 5B are schematic representations of the system.
Figure 5B:
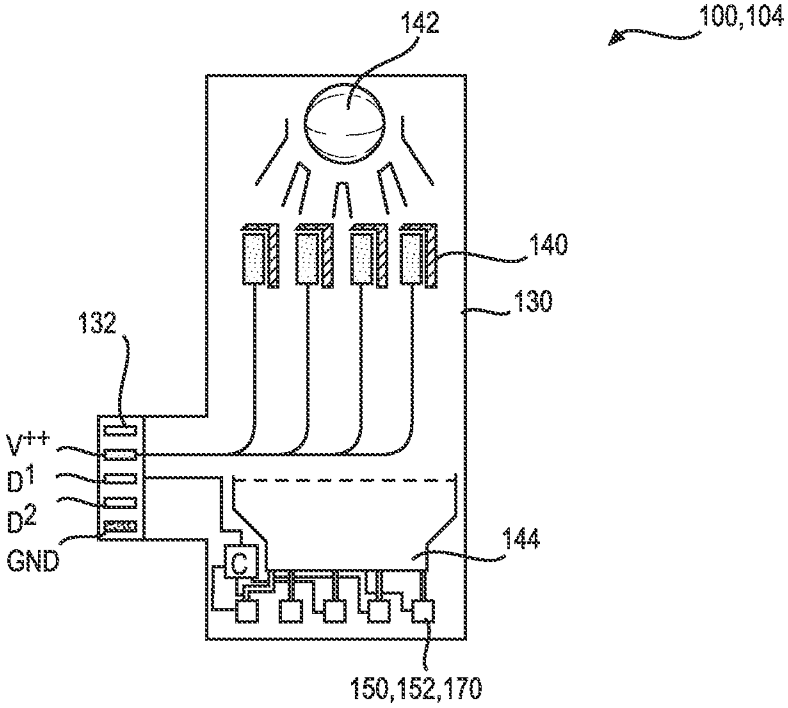
Figure 6A:
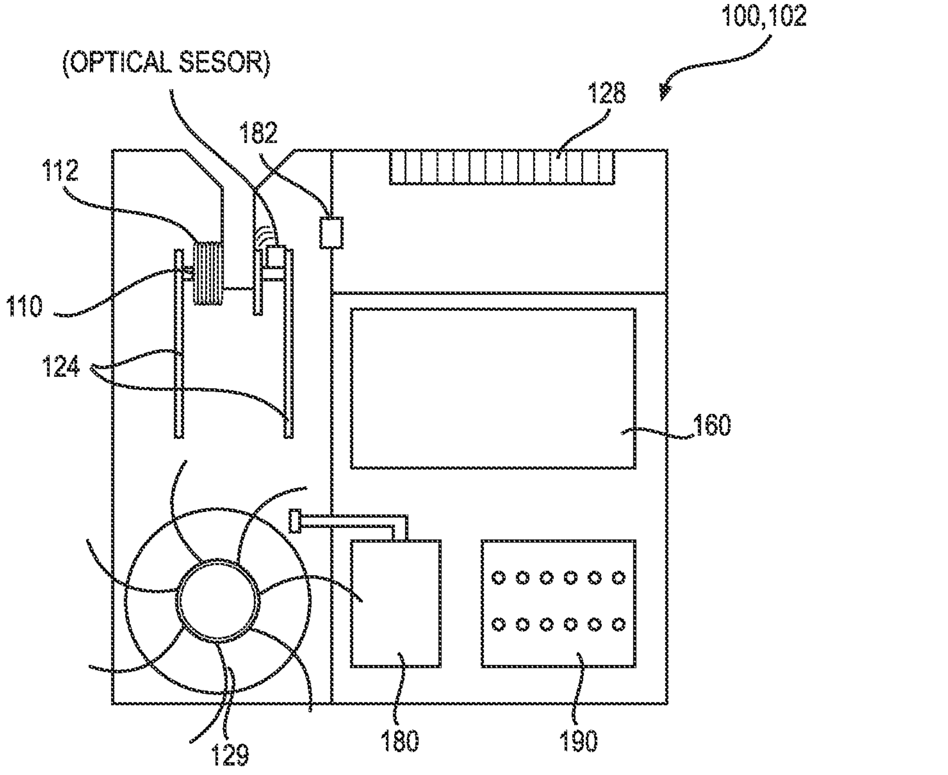
FIGS. 6A and 6B are schematic representations of the system.
Figure 6B:
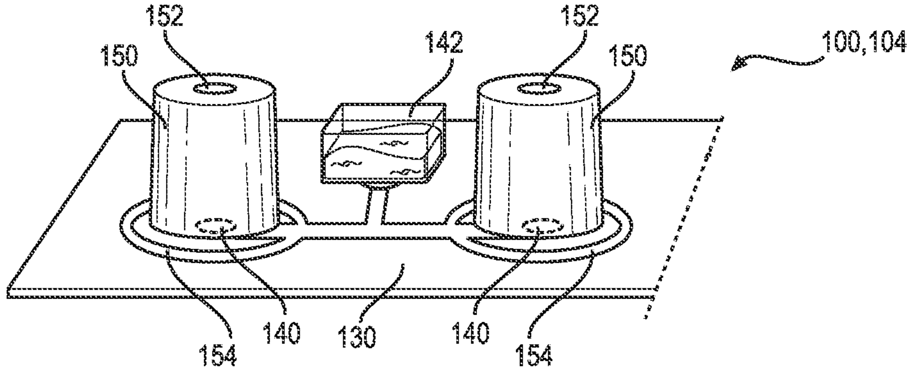
Figure 7:
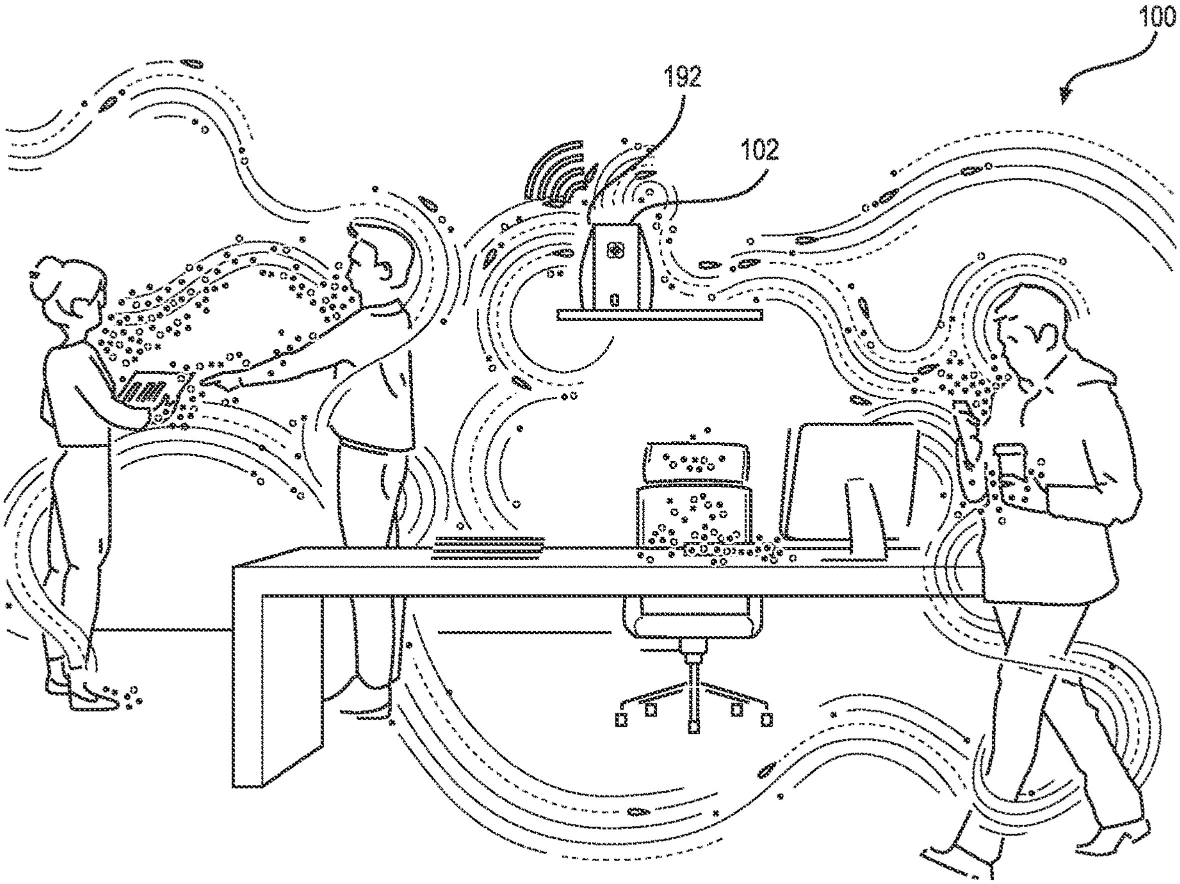
FIG. 7 is a schematic representation of the system.
Figure 8A:
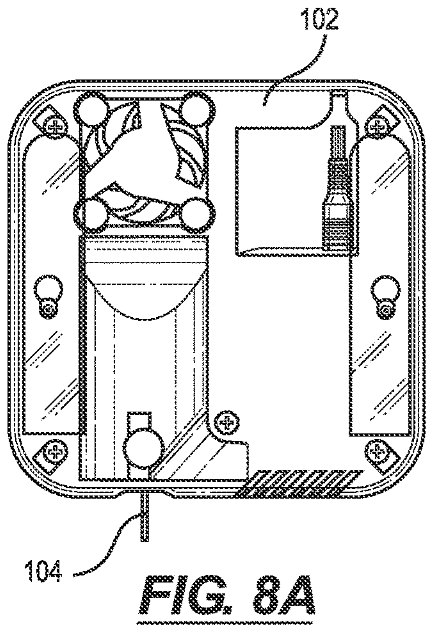
FIGS. 8A-8D are schematic representations of the system.
Figure 8B:
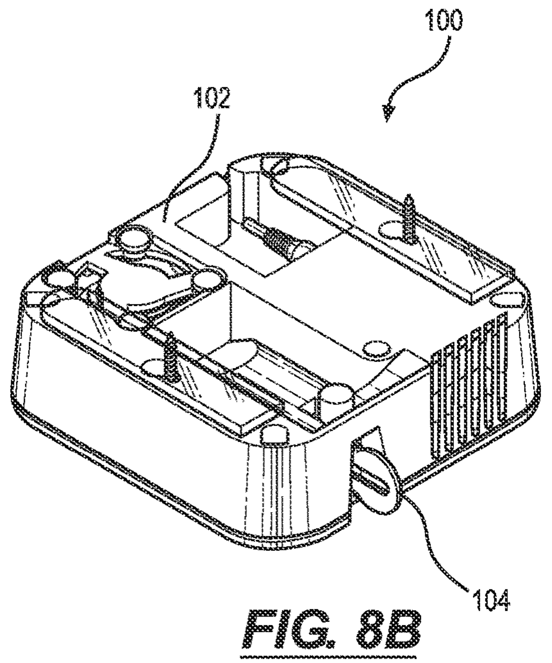
Figure 8C:
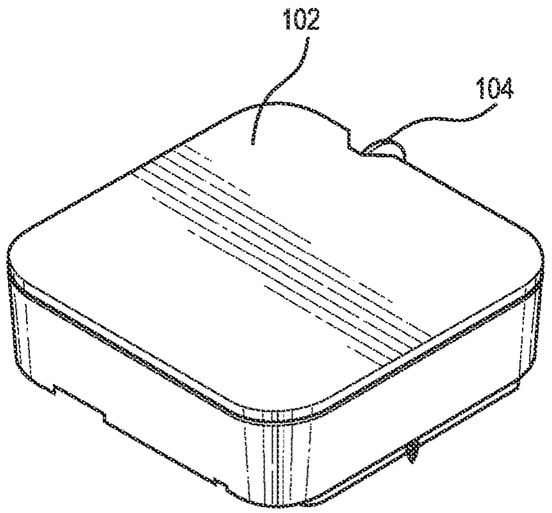
Figure 8D:
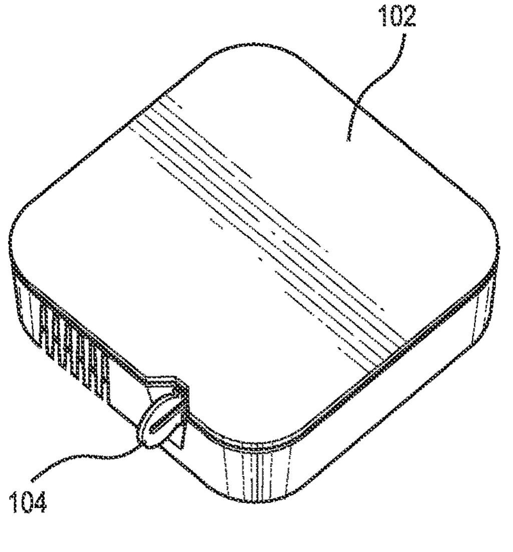
Figure 9A:
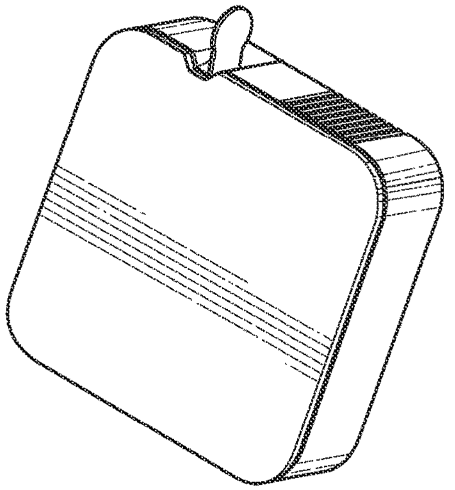
FIGS. 9A-9D are schematic representations of the system.
Figure 9B:
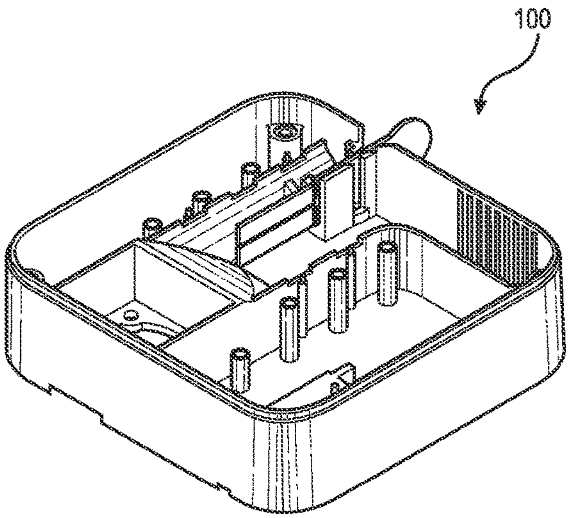
Figure 9C:
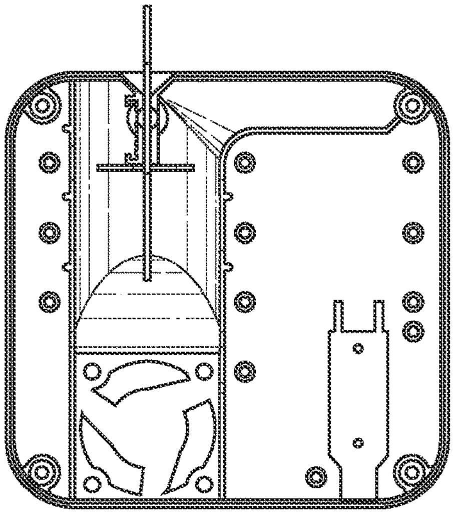
Figure 9D:
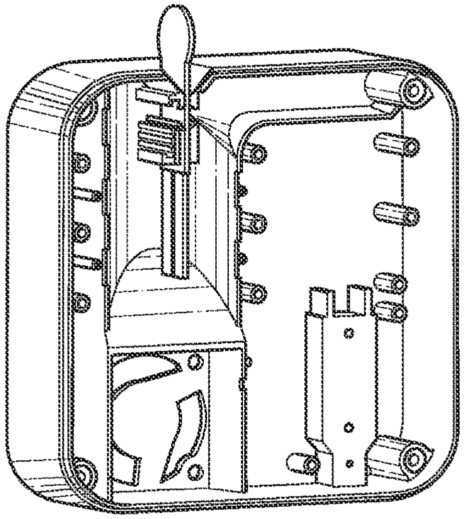
Figure 10A:
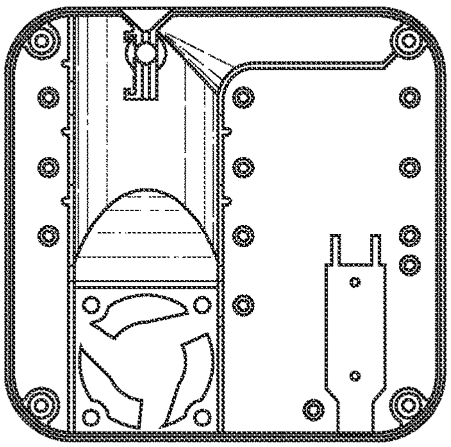
FIGS. 10A-10C are schematic representations of the system.
Figure 10B:
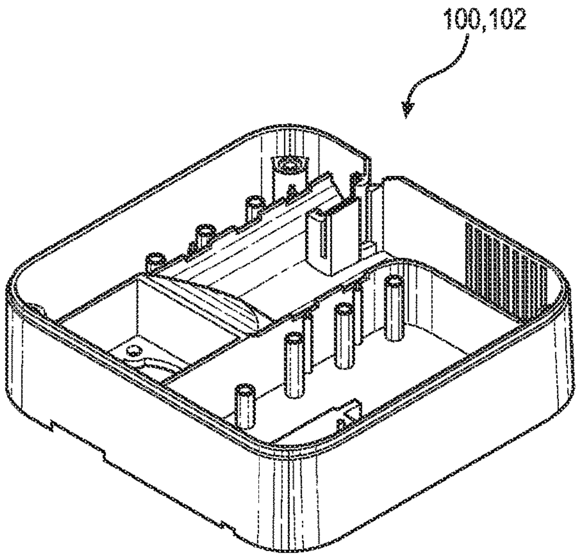
Figure 10C:
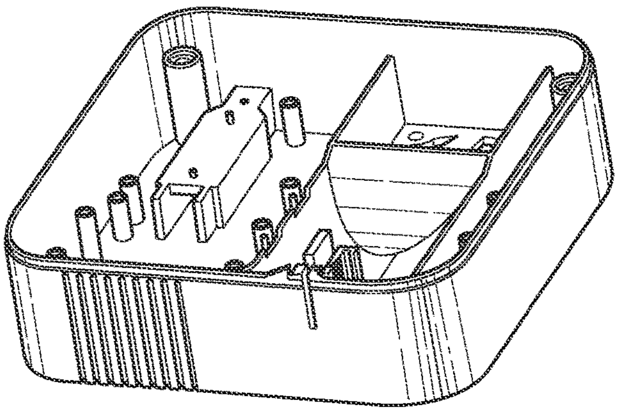
Figure 11A:
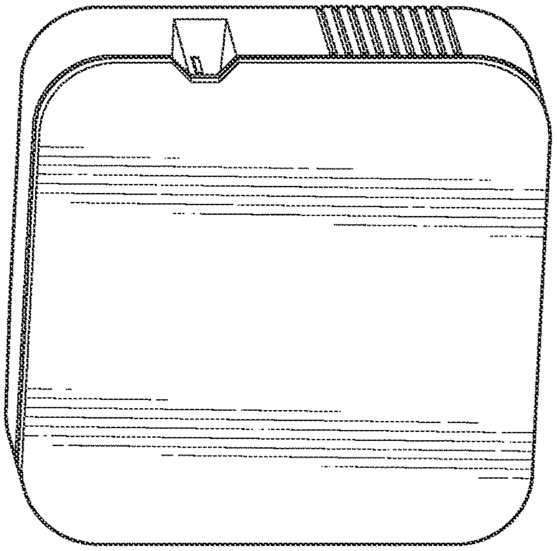
FIGS. 11A-11D are schematic representations of the system.
Figure 11B:
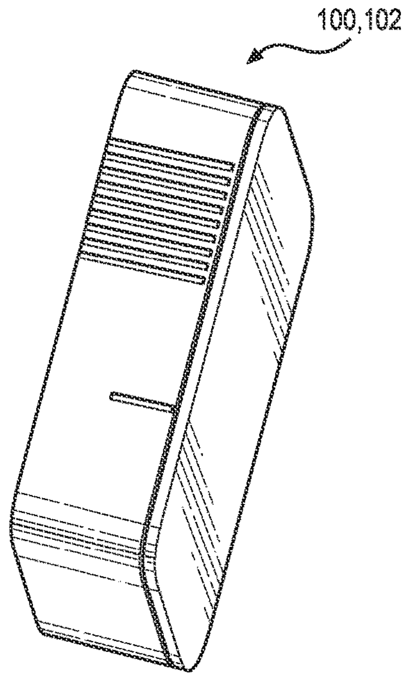
Figure 11C:
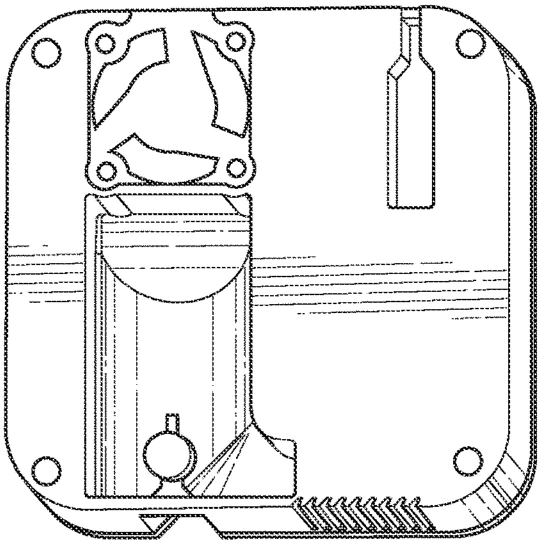
Figure 11D:
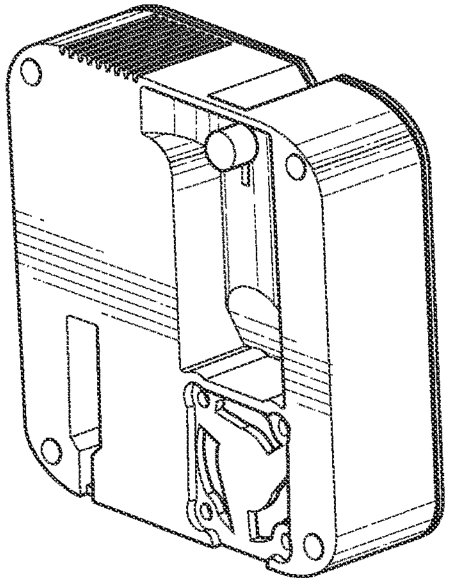

As shown in FIGS. 1A-1B, 2A-2B, 3, 4A-4B, 5A-5B, 6A-6B, 7, 8A-8D, 9A-9D, 10A-10C, and 11A-11D, a pathogen detection system 100 includes an air sampler 102 including: a housing 120; a tunnel 122 within the housing 120 and defining an inlet and an outlet 129; a set of charging elements 124 arranged within the tunnel 122 proximal the inlet; a cartridge receptacle 110 arranged proximal the outlet 129 and comprising a cartridge terminal 112; and a power supply 160 configured to drive a voltage between the set of charging elements 124 and the cartridge terminal 112. The pathogen detection system 100 further includes a cartridge 104 including: a substrate 130; a collector plate 140 arranged on the substrate 130 and configured to collect charged bioaerosols moving through the tunnel 122; and a connector 132 configured to transiently engage the cartridge receptacle 110 to locate the substrate 130 and the collector plate 140 within the tunnel 122 and electrically couple the collector plate 140 to the cartridge terminal 112.

In one variation, the pathogen detection system 100 further includes: a controller 190 comprising a set of electronics and configured to selectively actuate components of the air sampler 102; and a communication module 192 configured to transmit data between the air sampler 102, a set of external devices (e.g., a mobile device, a local computing device), and/or a computer system (e.g., a local server, a remote computer system).

One variation of the cartridge 104 further includes: a fluid reservoir 142 (e.g., a blister reservoir) arranged on the substrate 130 adjacent the collector plate 140 and preloaded with a volume of fluid; and a sample accumulator 144 arranged on the substrate 130 adjacent the collector plate 140, opposite the fluid reservoir 142, and configured to collect fluid and biological particulate flowing off of the collector plate 140. In this variation: the tunnel 122 defines the inlet 128 below the outlet 129; the cartridge receptacle 110 locates the cartridge 104 within the tunnel 122, above the charge electrode 124, and with the fluid reservoir 142 arranged over the collector plate 140; and the power supply 160 drives the voltage potential between the charge electrode 124 and the cartridge terminal 112 to electrically charge bioaerosols entering the inlet 128 of the tunnel 122 and to induce flow of electrically-charged bioaerosols from the charge electrode 124 onto the collector plate 140 of the cartridge 104.

In the preceding variation, the cartridge 104 can further include: a set of sensors 170 configured to detect pathogens in fluid; a manifold arranged on the substrate 130 adjacent the sample accumulator 144, opposite the collector plate 140, and configured to distribute fluid from the sample accumulator 144 to the set of sensors 170; and a databus coupling the set of sensors 170 to the cartridge receptacle 110. In this variation, the air sampler 102 further includes a controller 190 configured to: read a set of signals from the set of sensors 170 in the cartridge 104 via the databus, the cartridge receptacle 110, and the cartridge receptacle 110; and interpret levels of biological pathogens in air flowing through the tunnel 122 based on the set of signals.

One variation of the air sampler 102 further includes a fluid doser configured to dispense a volume of fluid onto the collector plate 140. In this variation, the cartridge 104 further includes a sample accumulator 144 arranged on the substrate 130 adjacent the collector plate 140 and configured to collect fluid and biological particulate flowing off of the collector plate 140. In this variation, the power supply 160 drives the voltage potential between the charge electrode 124 and the cartridge terminal 112 to electrically charge bioaerosols entering the inlet 128 of the tunnel 122 and to induce flow of electrically-charged bioaerosols from the charge electrode 124 onto the collector plate 140 of the cartridge 104. In this variation, the air sampler 102 further includes: a set of sensors 170 configured to detect pathogens in fluid; a manifold configured to distribute fluid from the sample accumulator 144 in the cartridge 104 to the set of sensors 170; and a controller 190 configured to read a set of signals from the set of sensors 170 and interpret levels of biological pathogens in air flowing through the tunnel 122 based on the set of signals.

Additionally and/or alternatively, one variation of the cartridge 104 further includes a set of fluidic channels containing a set of reagents matched to a predefined detection assay (e.g., a loop-mediated isothermal amplification assay) and fluidly coupled to the sample accumulator 144. In this variation, the air sampler 102 further includes: an optical sensor, arranged in the tunnel 122, facing the cartridge receptacle 110, and configured to capture an optical image of the set of the fluidic channels in the cartridge 104; and a controller 190 configured to interpret levels of pathogens in air flowing through the tunnel 122 based on optical signals (e.g., color changes) detected in the optical image.

One variation of the cartridge 104 further includes: a reaction chamber 150 fluidly coupled to the collector plate 140; a set of reagent reservoirs 152 loaded with a set of reagents corresponding to a defined detection assay and configured to release reagents, in the set of reagents, into the reaction chamber 150 according to the defined detection assay; and a set of heating elements 154 configured to regulate a temperature of the reaction chamber 150 according to the defined detection assay. In this variation, the air sampler 102 further includes an optical sensor arranged in the tunnel 122 and configured to record a set of optical signals generated by fluid in the reaction chamber 150 responsive to execution of the defined detection assay, the set of optical signals representative of presence of a set of pathogens in fluid within the reaction chamber 150.

One variation of the air sampler 102 further includes a cleaning module configured to sanitize surfaces within the tunnel 122 in preparation for a sampling period.

One variation of the pathogen detection system 100 includes an air sampler 102 including: a housing 120; a tunnel 122 within the housing 120 defining an inlet 128 and an outlet 129; a set of charging elements 124 arranged within the tunnel 122 proximal the inlet 128; a cartridge receptacle 110 arranged proximal the outlet 129 and including a cartridge terminal 122; and a power supply 160 configured to drive a voltage between the set of charging elements 124 and the cartridge terminal 112. In this variation, the pathogen detection system 100 includes a cartridge 104 including: a substrate 130; a set of collector plates 140 arranged on the substrate 130, each collector plate 140, in the set of collector plates 140, configured to collect pathogen samples of charged bioaerosols moving through the tunnel 122; a connector 132 configured to transiently engage the cartridge receptacle 110 to locate the substrate 130 within the tunnel 122 and electrically couple the set of collector plates 140 to the cartridge terminal 112; and a set of sensors 170 configured to generate a set of signals representing presence of a set of pathogens in pathogen samples; and a controller 190 configured to interpret presence of a set of pathogens in air flowing through the tunnel 122 based on the set of signals.

One variation of the pathogen detection system 100 includes an air sampler 102 including: a housing 120; a tunnel 122 within the housing 120 and defining an inlet 128 and an outlet 129; a charge electrode 124 arranged within the tunnel 122 proximal the inlet 128; a cartridge receptacle 110 arranged proximal the outlet 129 and comprising a cartridge terminal 112; and a power supply 160 configured to drive a voltage between the charge electrode 124 and the cartridge terminal 112. In this variation, the pathogen detection system 100 further includes a cartridge 104 including: a substrate 130; a collector plate 140 arranged on the substrate 130 and configured to collect charged bioaerosols moving through the tunnel 122; and a connector 132 configured to transiently engage the cartridge receptacle 110 to locate the substrate 130 and the collector plate 140 within the tunnel 122 and electrically couple the collector plate 140 to the cartridge terminal 112.

1.1 Pathogen Detection System: Set of Cartridges

One variation of the pathogen detection system 100 includes: the air sampler 102; and a set of cartridges 104. In this variation, each cartridge 104, in the set of cartridges 104, is configured to be loaded into the air sampler 102 during a particular sampling period, in a sequence of sampling periods, and includes: a substrate 130; a collector plate 140 arranged on the substrate 130 and configured to collect charged bioaerosols moving through the tunnel 122; and a connector 132 configured to transiently engage the cartridge receptacle 110 to locate the substrate 130 and the collector plate 140 within the tunnel 122 and electrically couple the collector plate 140 to the cartridge terminal 112.

2. Applications

Generally, the pathogen detection system 100 includes an air sampler 102 configured to: draw air from an enclosed environment (e.g., an enclosed space within a commercial, retail, office, or industrial building) into the air sampler 102 to collect pathogen samples via electrostatic forces; and detect pathogens present in the pathogen sample via genetic testing techniques. In particular, the air sampler 102 is configured to receive a cartridge 104, including a collector plate 140, to collect pathogen samples on this collector plate 140 during a sampling period. The cartridge 104 can then be replaced between sampling periods to insert a new collector plate 140 into the air sampler 102.

In particular, once deployed (e.g., permanently or temporarily installed) in a particular space, the air sampler 102 can ingest air from the space over time and draw this air over an internal collection subsystem to collect pathogen samples from the space, such as once per day, once per hour, once per minute, or continuously. An internal genetic material load detector 182, selective pathogen detector, or DNA sequencer 180 within the air sampler 102 can then process these pathogen samples to detect presence and/or magnitude (e.g., pathogen level) of various genetic material (or viral and/or bacterial pathogens specifically) in the space, and the air sampler 102 can then assemble detected presence and/or magnitudes of genetic material thus detected in the space over time into pathogen data representing presence and/or magnitude of genetic material in air within the space (e.g., at a particular time and/or over time). Alternatively, pathogen samples collected by the air sampler 102 can be intermittently returned to a lab for processing and diagnostics, such as by: removing a first cartridge 104—including a first collector plate 140 containing a first pathogen sample—from the air sampler 102; installing a second cartridge 104 into the air sampler 102 in preparation for a next air capture period; and returning the first cartridge 104 to the lab for remote processing.

Therefore, the pathogen detection system 100 can be deployed inside an office, a restaurant, a museum, a transportation terminal, a home, a venue, and/or other indoor, enclosed, or semi-enclosed environment to: rapidly detect rises in airborne microbe levels; quickly detect presence and levels of particular pathogens of interest (e.g., up to five high-risk bacterium or viruses); and detect presence of all airborne microbes (at concentrations above a minimum detectable level).

2.1 Sample Capture, Enrichment, and Processing

The air sampler 102 can include: an air-capture module configured to draw air from the enclosed environment into the air sampler 102 to concentrate a pathogen sample on a collector plate 140; and a detection module configured to enable diagnostics and/or genetic sequencing of the captured pathogen sample directly within the air sampler 102. In particular, the air capture module can include: a tunnel 122 extending from an inlet 128 of the air sampler 102 to an outlet 129 of the air sampler 102; a charging stage—proximal the inlet 128 within the tunnel 122—configured to generate an electrical field and thereby charge air flowing through the tunnel 122; a collector stage—downstream the charging stage within the tunnel 122—configured to direct charged particles (e.g., pathogens) in the air onto a conductive surface of a collector plate 140; and a cartridge receptacle 110 arranged proximal the outlet 129 and including a cartridge terminal 112.

The air sampler 102 can be configured to receive a replaceable (e.g., disposable) cartridge 104 including: a substrate 130 (e.g., a printed circuit board); a collector plate 140 (e.g., a conductive surface) arranged on the substrate 130; and a connector 132 (e.g., a USB connector) configured to transiently engage the cartridge receptacle 110, to locate the substrate 130 and the collector plate 140 within the tunnel 122, and to electrically couple the collector plate 140 to the cartridge terminal 112.

By collecting pathogen samples via electrostatic precipitation, the air sampler 102: excludes internal physical features that may impede airflow over a collector plate 140; and includes few or no moving parts, thereby reducing or eliminating noise and enabling the air sampler 102 to silently collect, enrich, and/or process a pathogen sample. Therefore, the air sampler 102 can be installed in a space (e.g., an office, a classroom) without causing disruption to the space due to noise generated by the air sampler 102 or increasing a noise floor within the space.

In one implementation, the collector plate 140 can be formed on a printed circuit board (e.g., a flexible or rigid printed circuit board). The printed circuit board can be configured for disposal after a sampling period such that, prior to each sampling period, a new printed circuit board—including a new or sanitized collector plate 140—is loaded into the cartridge receptacle 110 within the tunnel 122 for collection of a pathogen sample during a next sampling period. By forming the collector plate 140 on a printed circuit board, all electronic components of an electrostatic air capture system—other than a set of charge electrodes 124 and a power supply 160—can be integrated within a single plane within the air sampler 102, thereby simplifying construction of the air sampler 102 and minimizing elements impeding air flow within the tunnel 122. Further, by integrating electrical components of the air-capture module in a printed circuit board, many printed circuit boards can be generated quickly for continued use of the air sampler 102 in a particular space over time. Thus, the air sampler 102 is scalable for spaces of different sizes, which may require sampling periods of varying lengths, and/or more or less frequent air sampling.

3. Air Sampler

The pathogen detection system 100 includes an air sampler 102 configured to draw air from an external environment (e.g., surrounding the air sampler 102) into the air sampler 102 to extract pathogen samples from the air. Generally, the air sampler 102 is configured to transiently or semi permanently install in a particular environment (e.g., an enclosed space within a building). The air sampler 102 can cooperate with a cartridge 104—loaded in the air sampler 102—to directly sample air from this environment and locally (and/or remotely) implement pathogen detection.

In particular, the air sampler 102 is configured to: ingest a stream of ambient air from the external environment containing the air sampler 102—such as a conference room within an office building, a classroom within a school, and/or a waiting room within a hospital—into a tunnel 122 within the air sampler 102 via electrostatic forces; and cooperate with the cartridge 104 to collect a pathogen sample including charged bioaerosols—extracted from the stream of ambient air flowing through the tunnel 122—onto the collector plate 140 for detection of a set of pathogens (e.g., SARS-COV-2, Influenza A, *Salmonella*) in this pathogen sample.

In one implementation, the pathogen detection system 100 can include multiple air samplers 102 installed (e.g., transiently and/or semi-permanently installed) throughout a facility. In particular, in this implementation, the pathogen detection system 100 can include a set of air samplers 102 distributed throughout a facility, each air sampler 102, in the set of air samplers 102, installed in a particular environment (e.g., a particular room, floor, area, zone) within the facility and configured to ingest ambient air to collect pathogen samples in the particular environment to enable detection of a set of pathogens in the particular environment.

For example, the pathogen detection system 100 can include: a first air sampler 102 installed in a first defined space (e.g., a conference room), in a set of defined spaces, within a facility (e.g., an office building); and a second air sampler 102 installed in a second defined space (e.g., a break room), in the set of defined spaces, within the facility. In this example, the first air sampler 102 can be configured to: ingest a stream of ambient air from the first defined space into a first tunnel 122 of the first air sampler 102; and cooperate with a first cartridge 104—seated within a first cartridge receptacle 110 of the first air sampler 102—to collect pathogen samples representative of ambient air in the first defined space. Further, in this example, the second air sampler 102 can be configured to: ingest a stream of ambient air from the second defined space into a second tunnel 122 of the second air sampler 102; and cooperate with a second cartridge 104—seated within a second cartridge receptacle 110 of the second air sampler 102—to collect pathogen samples representative of ambient air in the second defined space.

Additionally, in this implementation, the pathogen detection system 100 can be configured to selectively activate each air sampler 102, in the set of air samplers 102, according to a fixed and/or dynamic sampling schedule.

3.1 Housing

The air sampler 102 can include a housing 120 defining a body or "chassis": configured to support and locate a combination of air-capture and detection modules, a controller 190, and/or a communication module 192; configured for transport within a facility—including the particular environment—for reinstallation at a different location within the facility or within a remote facility (e.g., a laboratory) for maintenance and/or reassembly; configured to install in the particular environment (e.g., an office, a classroom, a restaurant) with minimal disruption to the particular environment; and configured to enable replacement of components or modules contained within the housing 120. For example, the housing 120 can define a rigid body including features for: fixing to a wall or to a surface (e.g., a surface of a table) within the particular environment; transport within the facility; and enabling access to components contained within the housing 120.

The air sampler 102 can include a tunnel 122 defining: an inlet 128 configured to pass air—including pathogens—from the environment into the tunnel 122; and an outlet 129 configured to release air and uncharged particles in the air from within the air sampler 102 and back into the external environment. The inlet 128 and the outlet 129 can be arranged on surfaces of the housing 120, such that the tunnel 122 extends between surfaces of the housing 120. In particular, the inlet 128 and the outlet 129 can be arranged on the housing 120 such that the tunnel 122 defines a particular pathway for airflow that enables air to flow through the tunnel 122 with minimal blockage. In one implementation, the tunnel 122 can include an air flow straightener (e.g., a honeycomb screen) arranged proximal the inlet 128 of the tunnel 122.

The housing 120 can also include a set of openings 126 (e.g., doors and/or windows) to access and/or view various modules and/or components of the air sampler 102.

In one implementation, the housing 120 includes an opening 126: arranged on the housing 120 proximal the cartridge terminal 112; and configured to transiently receive the cartridge 104 to seat the cartridge 104 within the cartridge receptacle 110. For example, the housing 120 can include a door 126 configured to enable user access to the cartridge receptacle 110 housed within the tunnel 122, such that a user may open the door 126 to insert and/or remove a collector plate 140 between sampling periods. Additionally and/or alternatively, in this example, the door 126 can include an interrupt assembly, such that when the door 126 is open, the power supply 160 to the air-capture module is disabled.

Additionally, the housing 120 can include a cap configured to fit over the inlet 128 during inactive periods between sampling periods. Further, in one implementation, the housing 120 can include a vent arranged across the inlet 128 of the tunnel 122 to prevent user access to the tunnel 122 via the inlet 128. The vent can be configured to enable air flow (e.g., including particles in the air) through the gate while preventing larger bodies (e.g., human fingers) from entering the inlet 128.

3.1.1 Alert Features

In one variation, the air sampler 102 can include a set of alert features arranged on the housing 120 and configured to convey information—such as related to the air sampler 102 and/or the environment containing the air sampler 102—to a human user. For example, the air sampler 102 can include a set of lights arranged on the housing 120. The air sampler 102 and/or the controller 190 can selectively activate the set of lights—individually and/or in combination—to provide information regarding the air sampler 102 and/or the environment to users proximal the air sampler 102.

For example, the air sampler 102 can include a set of alert features including: a continuous green light arranged on the housing 120 and configured to activate during sampling periods and deactivate between sampling periods; a continuous red light arranged on the housing 120 and configured to activate responsive to detecting a particular pathogen present in the environment containing the air sampler 102; and a flashing yellow light configured to activate to prompt a user or users in the environment to replace the cartridge 104 loaded in the air sampler 102 with a new cartridge 104.

3.2 Charging Stage

The air sampler 102 includes a charging stage—integrated within the tunnel 122—configured to draw air from the environment through the inlet 128 of the tunnel 122 via electrostatic forces for collection of a pathogen sample onto a collector plate 140 inserted into the tunnel 122 of the air sampler 102. In particular, the air sampler 102 can include a charging stage including: a charge electrode 124 arranged within the tunnel 122 proximal the inlet 128; and a cartridge receptacle 110 proximal the outlet 129 and including a cartridge terminal 112 (e.g., a USB port). The air sampler 102 can further include a power supply 160 configured to drive a voltage potential between the charge electrode 124 and the cartridge terminal 112. The charge electrode 124 and the cartridge terminal 112 can be configured to hold a high voltage arc (e.g., 2,000 Volts to 20,000 Volts), therefore enabling generation of a high voltage electrical field. Thus, when the power supply 160 is activated, the charge electrode 124 and the cartridge terminal 112 can cooperate to generate an electric field extending between the charge electrode 124 and the cartridge terminal 112 within the tunnel 122, thereby charging particles in air flowing through the tunnel 122.

In one implementation, the charge electrode 124 can include a wire (e.g., a Tungsten wire) arranged within the tunnel 122 proximal the inlet 128. Additionally and/or alternatively, the charge electrode 124 can include an array of wires arranged within the tunnel 122 and configured to cooperate with the cartridge terminal 112 to generate an electrical field across the tunnel 122.

In one implementation, the charge electrode 124 can be configured to receive a negative voltage. In this implementation, the cartridge terminal 112 can be configured to receive a positive charge to generate the electrical field between the charge electrode 124 and the cartridge terminal 112. Alternatively, in another implementation, the charge electrode 124 can be configured to receive a positive voltage and the cartridge terminal 112 can be configured to receive a negative charge to generate the electrical field between the charge electrode 124 and the cartridge terminal 112.

In one implementation, the charging stage can also include a heating element 154 arranged proximal the outlet 129 of the tunnel 122 downstream of the cartridge receptacle 110, opposite the charge electrode 124. The heating element 154 can be configured to promote air flow from the external environment surrounding the air sampler 102, into the inlet 128, and through the tunnel 122, thereby increasing a velocity of airflow through the tunnel 122 without implementation of a noise-generating device, such as a pump or a fan.

3.3 Cleaning Module

The air sampler 102 can also include a cleaning module configured to sanitize surfaces of the charging stage (e.g., the tunnel 122, the charge electrode 124, the cartridge receptacle 110) in between sampling periods to minimize contamination of pathogen samples collected. For example, the air sampler 102 can include a UV light configured to activate between sampling periods—such as before loading of the air sampler with a new (dean) cartridge—to sanitize interior surfaces of the air sampler (e.g., including surfaces of the air-capture module). In this example, the air sampler 102 (and/or a controller 190) can selectively actuate the UV light before and/or after each sampling period to sanitize these surface and therefore minimize contamination of pathogen samples collected during a subsequent sampling period.

3.4 Controller

In one variation, the air sampler 102 can include a controller 190 including a set of electronics and configured to selectively actuate components of the air sampler 102 to enable collection of pathogen samples within the air sampler 102 and/or detection of pathogens in these pathogen samples.

Additionally, in another variation, the controller 190 can be configured to track a timeseries of bioaerosol collection data to assemble a pathogen sample record (or "sample record") for the air sampler 102. For example, the controller 190 can be configured to: trigger initiation of a first sampling period at the air sampler 102 at a first time; record a first time value (e.g., a timestamp) corresponding to the first time; and selectively actuate components of the air sampler 102 to collect a first pathogen sample on a first collector plate 140 loaded in the tunnel 122 of the air sampler 102 during the first sampling period. Then, at a second time, in response to expiration of the sampling period, the controller 190 can: record a second time value corresponding to the second time; access a first pathogen level (e.g., detected by a sensor proximal the first collector plate 140) of a first pathogen present in the first pathogen sample; and generate a first sample record for the first pathogen sample collected during the first sampling period based on the first time value, the second time value, and the first pathogen level. The controller 190 can then repeat this process to generate a time-series of sample records, each sample record corresponding to a particular pathogen sample collected during a particular sampling period.

3.5 Communication Module

The pathogen detection system 100 can be configured to communicate data (e.g., pathogen levels, pathogen identity) between connected devices and/or to a set of users associated with the environment in which the air sampler 102 is installed. In particular, the pathogen detection system 100 can include a communication module 192 (e.g., coupled to the controller 190) configured to transmit data and/or notifications to a remote server and/or a set of local devices associated with the set of users.

For example, the air sampler 102 can include a wireless transceiver configured to connect to a set of wireless devices and to transmit various data to these devices from the air sampler 102. In particular, in this example, the air sampler 102 can connect to a user's smartphone or tablet—executing a native pathogen tracking application—to deliver notifications and/or updates on pathogen levels and/or pathogens identified in the environment.

Additionally and/or alternatively, in another example, the air sampler 102 can be configured to deliver notifications and/or updates regarding sampling periods and cartridge 104 replacement. In particular, in one example, the air sampler 102—loaded with a first cartridge 104 including a first collector plate 140—can trigger initiation of a first sampling period for collection of a first pathogen sample on the first collector plate 140. Then, in response to expiration of the first sampling period, the communication module 192 (e.g., a wireless transceiver) can: generate a notification comprising a prompt to remove the first cartridge 104 from the cartridge receptacle 110 of the air sampler 102 and insert a second cartridge 104—including a second collector plate 140—into the cartridge receptacle 110 for collection of a second pathogen sample during a second sampling period; and transmit the notification to a user associated with an environment containing the air sampler 102 prior to initiation of the second sampling period.

4. Cartridge

The pathogen detection system 100 includes a cartridge 104 configured to couple with the air sampler 102, prior to a sampling period, to collect a pathogen sample on surfaces within the cartridge 104.

In particular, the cartridge 104 can include: a substrate 130 (e.g., a printed circuit board); a collector plate 140 arranged on the substrate 130 and configured to collect charged bioaerosols moving through the tunnel 122; and a connector 132 configured to transiently engage the cartridge receptacle 110, to locate the substrate 130 and the collector plate 140 within the tunnel 122, and to electrically couple the collector plate 140 to the cartridge terminal 112.

The cartridge 104 can be inserted into the tunnel 122 of the air sampler 102 prior to initiation of a sampling period during which air is drawn into the air sampler 102 for collection of a pathogen sample. Upon completion of the sampling period and/or prior to initiation of a next sampling period, the cartridge 104 can be removed from the air sampler 102 and replaced with a new cartridge 104 for collection of a next pathogen sample during the next sampling period. Therefore, the pathogen detection system 100 can include a set of cartridges 104, each cartridge 104, in the set of cartridges 104, including a substrate 130, a collector plate 140, and a connector 132, such that a pathogen sample can be collected within the cartridge 104. Further, these cartridges 104 can be configured for disposal after each sampling period. For example, the set of cartridges 104 can be formed of a disposable plastic material.

In one example, the pathogen detection system 100 can include a set of cartridges 104, each cartridge 104 in the set of cartridges 104 allocated for bioaerosol collection during a particular sampling period. In particular, in this example, the set of cartridges 104 can include a first cartridge 104: loaded with a first collector plate 140 configured to collect charged bioaerosols moving through the tunnel 122 of the air sampler 102 and arranged on a first substrate 130 (e.g., a first printed circuit board); including a first connector 132 configured to transiently engage the cartridge receptacle 110 to locate the first substrate 130 and the first collector plate 140 within the tunnel 122 and electrically couple the first collector plate 140 to the cartridge terminal 112; and allocated for bioaerosol collection during a first sampling period.

Further, in this example, the set of cartridges 104 can include a second cartridge 104: loaded with a second collector plate 140 configured to collect charged bioaerosols moving through the tunnel 122 of the air sampler 102 and arranged on a second substrate 130 (e.g., a second printed circuit board); including a second connector 132 configured to transiently engage the cartridge receptacle 110 to locate the second substrate 130 and the second collector plate 140 within the tunnel 122 and electrically couple the second collector plate 140 to the cartridge terminal 112; and allocated for bioaerosol collection during a second sampling period succeeding the first sampling period.

In this example, the air sampler 102 can be configured to: receive the first cartridge 104 within the cartridge receptacle 110—via coupling of the first connector 132 with the cartridge terminal 112—for collection of a first pathogen sample on the first collector plate 140 during the first sampling period; and receive the second cartridge 104, in replacement of the first cartridge 104, within the cartridge receptacle 110—via coupling of the second connector 132 with the cartridge terminal 112—for collection of a second pathogen sample during the second sampling period succeeding the first sampling period. Therefore, a user may: insert the first cartridge 104 into the air sampler 102 at a first time—preceding the first sampling period—in preparation for collection of the first pathogen sample during the first sampling period; remove the first cartridge 104 from the air sampler 102 in response to expiration of the first sampling period; and, at a second time—succeeding the first sampling period and preceding the second sampling period—insert the second cartridge 104 into the air sampler 102, in replacement of the first cartridge 104, in preparation for collection of the second pathogen sample during the second sampling period.

In the preceding example, the pathogen detection system 100 can also include: a third cartridge 104 allocated for collection of a third pathogen sample during a third sampling period; a fourth cartridge 104 allocated for collection of a fourth pathogen sample during a fourth sampling period; a fifth cartridge 104 allocated for collection of a fifth pathogen sample during a fifth sampling period; and so on.

The cartridge 104 can thus be configured for handling by a user (e.g., a non-skilled user), such that the user may physically manipulate the cartridge 104 to insert the collector plate 140 into the air sampler 102—and electrically connect the collector plate 140 with the cartridge receptacle 110—without any physical contact by the user or the external environment (e.g., ambient air). The cartridge 104 can therefore be configured to serve as a housing 120 for the collector plate 140 to enable safe handling (e.g., for the user) while minimizing contamination of the collector plate 140.

For example, the substrate 130—including the collector plate 140—can initially be loaded into a cartridge 104. A user may insert the cartridge 104 into the cartridge receptacle 110 via a door 126, on the housing 120 of the air sampler 102, configured to receive the cartridge 104. Once the cartridge 104 is inserted into the cartridge receptacle 110, the user may "eject" the substrate 130 from the cartridge 104—such as by clicking an eject button on the cartridge 104—to locate the substrate 130 and the collector plate 140 within the tunnel 122, and electrically connect the collector plate 140 with the cartridge terminal 112. In this example, once the collector plate 140 is electrically coupled with the cartridge terminal 112, the air sampler 102 and/or controller 190 can trigger initiation of a sampling period by actuating the power supply 160 of the air sampler 102. Then, upon completion of the sampling period and/or subsequent detection periods, the user may eject the substrate 130 and collector plate 140 from the cartridge receptacle 110 and back into the cartridge 104, such as by again clicking the eject button. The user may then deliver the cartridge 104—containing the dirty collector plate 140—to a designated location for further processing and/or proper disposal without any contact (e.g., physical contact of surfaces or airborne contact) between the user and the collected pathogen sample.

4.1 Substrate: Printed Circuit Board

In one implementation, the substrate 130 can be formed of a printed circuit board (e.g., a rigid or flexible printed circuit board). In particular, in this implementation, the pathogen detection system 100 can include the air sampler 102 and the cartridge 104 including: a printed circuit board; a collector plate 140 arranged on the printed circuit board and configured to collect charged bioaerosols moving through the tunnel 122; and a connector 132 configured to transiently engage the cartridge receptacle 110 to locate the printed circuit board and the collector plate 140 within the tunnel 122 and electrically couple the collector plate 140 to the cartridge terminal 112.

In this implementation, the printed circuit board (i.e., the substrate 130) can be configured to couple with the cartridge terminal 112 upon insertion into the tunnel 122. By integrating the collector plate 140 into a printed circuit board, the collector plate 140 can be configured to electrically connect to the cartridge terminal 112 via a circuit board trace (e.g., a copper trace) integrated into the printed circuit board. Further, by integrating the collector plate 140 into a printed circuit board, these electrical components can be arranged in a single plane (e.g., via traces on the printed circuit board), thereby eliminating additional wiring and/or connectors 132 for electrically coupling the collector plate 140 to the cartridge terminal 112 and therefore: minimizing a complexity of the cartridge 104 and/or air sampler 102 by reducing a number of distinct electrical components; and minimizing barriers to air flow within the tunnel 122 by locating electrical components in a single plane within the tunnel 122.

For example, the cartridge 104 can include: a printed circuit board including a set of circuit board traces (or "traces"); a collector plate 140 arranged on the printed circuit board; and a connector 132 configured to transiently engage the cartridge receptacle 110 of the air sampler 102 to electrically couple the collector plate 140 to the cartridge terminal 112 via a first trace, in the set of traces, extending between the connector 132 and the collector plate 140.

In another example, the cartridge 104 can include a flexible printed circuit board as the substrate 130. In this example, the printed circuit board can: define a primary plane (e.g., defined by a body of the printed circuit board); and include a set of collector plates 140 extending outward from (e.g., perpendicular to) the primary plane. In particular, to construct the set of collector plates 140, the printed circuit board can be perforated (e.g., in a C-shape) in a particular region to generate a foldable tab. This foldable tab can be bent upward (e.g., from the primary plane) to form a collector plate 140. The printed circuit board can be perforated multiple times to generate multiple collector plates 140 on the printed circuit board. The printed circuit board can be configured to include a set of traces (e.g., copper traces) running from the connector 132 to each collector plate 140 to electrically connect each collector plate 140, in the set of collector plates 140, to the cartridge terminal 112.

4.2 Collector Plate

The air sampler 102 can be configured to receive a substrate 130 including a collector plate 140 arranged on the substrate 130 and configured to collect and concentrate a pathogen sample for detection of pathogens within the pathogen sample. In particular, the collector plate 140 can be configured to electrically and mechanically connect to the cartridge receptacle 110 within the tunnel 122 of the housing 120 upon insertion into the air sampler 102.

The collector plate 140 can define a conductive surface configured to attract electrically charged particles from an air sample, flowing through the tunnel 122, onto a surface of the collector plate 140. Upon insertion of the collector plate 140 into the air sampler 102 and coupling of the collector plate 140 with the cartridge terminal 112, a voltage can be applied across the collector plate 140, thereby enabling the collector plate 140 to attract charged particles passing through the tunnel 122 (e.g., in an air sample). Uncharged particles in the air will pass over the collector plate 140 and exit the tunnel 122 via the outlet 129 for release back into the environment, while charged particles will collect on the collector plate 140.

4.2.1 Multiple Collector Plates

In one variation, the cartridge 104 can include multiple collector plates 140 (e.g., 2 collector plates 140, 10 collector plates 140, 100 collector plates 140) arranged on the substrate 130 (e.g., within the cartridge 104). In particular, in this variation, the cartridge 104 can include: a substrate 130; a set of collector plates 140 arranged on the substrate 130, each collector plate 140, in the set of collector plates 140, configured to collect charged bioaerosols moving through the tunnel 122; and a connector 132 configured to transiently engage the cartridge receptacle 110 to locate the substrate 130 and the set of collector plates 140 within the tunnel 122 and electrically couple the set of collector plates 140 to the cartridge terminal 112.

For example, the cartridge 104 can include: a substrate 130; a first collector plate 140 arranged on the substrate 130 and configured to collect charged bioaerosols moving through the tunnel 122; a second collector plate 140 arranged on the substrate 130 and configured to collect charged bioaerosols moving through the tunnel 122; and a connector 132 configured to transiently engage the cartridge receptacle 110 to locate the substrate 130, the first collector plate 140, and the second collector plate 140 within the tunnel 122 of the air sampler 102 and electrically couple the first collector plate 140 and the second collector plate 140 to the cartridge terminal 112. Additionally and/or alternatively, in another example, the cartridge 104 can include an array of collector plates 140 (e.g., five, ten, or 100 collector plates 140) arranged on the substrate 130 (e.g., a printed circuit board) within the cartridge 104.

4.2.1.1 Multiple Collector Plates: Multiple Sampling Periods

In one implementation, the cartridge 104 can include a set of collector plates 140 arranged on the substrate 130, each collector plate 140 in the array configured to be activated during a particular sampling period.

For example, the cartridge 104 can include: a substrate 130; a first collector plate 140 arranged on the substrate 130 and configured to collect charged bioaerosols moving through the tunnel 122 of the air sampling during a first sampling period; and a second collector plate 140 arranged on the substrate 130 and configured to collect charged bioaerosols moving through the tunnel 122 during a second sampling period (e.g., offset the first sampling period and/or succeeding the first sampling period).

In this example, the controller 190 can: activate the first collector plate 140—such as by triggering electrical coupling of the cartridge terminal 112 to the first collector plate 140 (e.g., via a first circuit board trace extending between the connector 132 and the first collector plate 140)—for collection of a first pathogen sample on the first collector plate 140 during the first sampling period; and activate the second collector plate 140—such as by triggering electrical coupling of the cartridge terminal 112 to the second collector plate 140 (e.g., via a second circuit board trace extending between the connector 132 and the second collector plate 140)—for collection of a second pathogen sample on the second collector plate 140 during the second sampling period. The pathogen detection system 100 can therefore selectively activate collector plates 140 loaded in the tunnel 122 during corresponding sampling periods by selectively coupling the collector plates 140 with the power supply 160.

Additionally and/or alternatively, in another example, the controller 190 can be configured to load a particular collector plate 140, in a set of collector plates 140, into a sampling position on the substrate 130. The cartridge receptacle 110 can therefore be configured to electrically couple the collector plate 140, loaded in the sampling position, to the cartridge terminal 112. In particular, in one example, the set of collector plates 140 can be arranged on a rotating disk. In this example, the air sampler 102 and/or controller 190 can: locate a first collector plate 140, in the set of collector plates 140, within the sampling position; trigger collection of a first pathogen sample onto the first collector plate 140—loaded in the sampling position—during a first sampling period; in response to expiration of the first sampling period, trigger rotation of the disk to locate a second collector plate 140, in the set of collector plates 140, in the sampling position; and trigger collection of a second pathogen sample onto the second collector plate 140—loaded in the sampling position—during a second sampling period succeeding the first sampling period.

In another example, the cartridge 104 can include an array of 10 collector plates 140 arranged on a printed circuit board. Each day, the controller 190 can trigger the power supply 160 to electrically couple a particular collector plate 140, in the array of 10 collector plates 140, to the cartridge terminal 112. In particular, on a first day, the controller 190 can trigger the power supply 160 to electrically couple a first collector plate 140 to the cartridge terminal 112, via a first trace in the printed circuit board. On a second day, the controller 190 can trigger the power supply 160 to electrically couple a second collector plate 140 to the cartridge terminal 112, via a second trace in the printed circuit board, and so on. After 10 days, a user associated with the air sampler 102 may remove the cartridge 104 from the air sampler 102 and insert a new cartridge 104 including a new array of 10 collector plates 140.

4.2.1.2 Multiple Collector Plates: Multiple Pathogens

Additionally and/or alternatively, in another implementation, the cartridge 104 can include a set of collector plates 140 arranged on the substrate 130, each collector plate 140 in the set of collector plates 140 configured to collect a pathogen sample matched to a particular pathogen and/or detection assay.

For example, the cartridge 104 can include: a substrate 130; a first collector plate 140 arranged on the substrate 130 and configured to collect charged bioaerosols moving through the tunnel 122; and a second collector plate 140 arranged on the substrate 130 and configured to collect charged bioaerosols moving through the tunnel 122; and a connector 132 configured to transiently engage the cartridge receptacle 110 to locate the substrate 130, the first collector plate 140, and the second collector plate 140 within the tunnel 122 of the air sampler 102 and to electrically couple the first collector plate 140 and the second collector plate 140 to the cartridge terminal 112. Additionally, in this example, the cartridge 104 can further include: a first sensor (e.g., a biosensor, a colorimetric test strip)—arranged proximal the first collector plate 140 (e.g., on a surface of the first collector plate 140 and/or substrate 130)—configured to detect presence of a first pathogen, in a set of pathogens, in pathogen samples; and a second sensor—arranged proximal the second collector plate 140 (e.g., on a surface of the first collector plate 140 and/or substrate 130)—configured to detect presence of a second pathogen, in the set of pathogens, in pathogen samples.

In this example, the air sampler 102 and/or controller 190 can activate the first collector plate 140 and the second collector plate 140—such as by electrically coupling the first collector plate 140 to the cartridge terminal 112 (e.g., via a first electrical trace on the substrate 130) and electrically coupling the second collector plate 140 to the cartridge terminal 112 (e.g., via a second electrical trace on the substrate 130)—during a sampling period, such that charged bioaerosol particles flowing through the tunnel 122 collect on surfaces of both the first and second collector plate 140 during the sampling period. The pathogen detection system 100 can therefore collect multiple pathogen samples during a singular sampling period in order to enable detection of multiple pathogens by a set of sensors 170 configured to detect a set of pathogens.

4.3 Variation: Substrate+Collector Plate

In one variation, the substrate 130 (e.g., a printed circuit board), including the collector plate 140, can be directly inserted into the tunnel 122 to engage the cartridge receptacle 110, without the cartridge 104. For example, the user may open a door 126 in the housing 120 to insert the substrate 130 directly into the tunnel 122. The user may then manually connect a connector 132 on the substrate 130 to the cartridge terminal 112 in the tunnel 122 to electrically couple the collector plate 140 to the cartridge terminal 112. In this example, once the user closes the door 126 to the housing 120, the air sampler 102 and/or controller 190 can activate a cleaning module (e.g., a UV light) within the tunnel 122 to sanitize surfaces of the substrate 130 and/or collector plate 140. Then, the air sampler 102 and/or controller 190 can initiate a sampling period by triggering the power supply 160 to drive a voltage between the charge electrode 124 and the cartridge terminal 112. Upon completion of the sampling period, the user may insert a swab through a sampling window in the housing 120 proximal the collector plate 140 to extract a pathogen sample from the surface of the collector plate 140. The user may then store this swab in a sample container (e.g., a sterile tube) for storage and detection of pathogens in the pathogen sample at a remote location.

5. Hydrophobic Fluid Reservoir

In one variation, the collector plate 140 can be configured to receive a volume of a hydrophobic fluid (e.g., a saline solution) before or after a sampling period to enable detection of pathogens present in charged bioaerosols collected on the collector plate 140 during the sampling period. Microbial pathogen samples can thus be concentrated within this liquid for collection rather than collecting pathogen samples (e.g., dry pathogen samples) directly from the surface of the collector plate 140, thereby enabling post-processing of these microbial pathogen samples for (near) real-time pathogen detection.

In one implementation, the air sampler 102 can include a fluid reservoir 142 configured to store a volume of hydrophobic fluid for dispensation onto the collector plate 140. The air sampler 102 can include: a fluid reservoir 142 loaded with a volume of the hydrophobic fluid (e.g., a saline solution); and a fluid doser (e.g., fluid dispenser) configured to dispense a set volume (e.g., a single drop) of the hydrophobic fluid from the fluid reservoir 142 and across the surface of the collector plate 140. In this implementation, the fluid doser can be arranged over the collector plate 140 within the tunnel 122, such that dispenser releases the hydrophobic fluid onto a particular region of the collector plate 140. Additionally, in this implementation, the cartridge 104 can include a sample accumulator 144 arranged on the substrate 130 adjacent the collector plate 140 and configured to collect fluid and biological particular flowing off the collector plate 140.

For example, the air sampler 102 and/or controller 190 can trigger the fluid doser to dispense the set volume of the hydrophobic fluid onto the surface of the collector plate 140 upon termination of a sampling period, prior to analysis of the pathogen sample collected on the collector plate 140. The dispensed volume of the hydrophobic fluid can roll across the surface of the collector plate 140 and flow into the sample accumulator 144 for further processing. In this example, a user associated with the air sampler 102 may periodically (e.g., prior to each sampling period, after a threshold quantity of sampling periods, once per week) refill the fluid reservoir 142 within the air sampler 102.

In another implementation, the cartridge 104 can be configured to store a preset volume of the hydrophobic fluid for dispensation onto the collector plate 140. The cartridge 104 can include a fluid reservoir 142 (e.g., a blister reservoir) prefilled with a set volume of the hydrophobic fluid and coupled to the collector plate 140. In this implementation, the air sampler 102 can include a blister plunger arranged over the fluid reservoir 142—when the collector plate 140 is installed within the tunnel 122—and configured to pierce (e.g., penetrate) the fluid reservoir 142 to release the hydrophobic fluid from within the reservoir and onto the surface of the collector plate 140. In this implementation, the cartridge 104 can further include: a sample accumulator 144 arranged on the substrate 130 adjacent the collector plate 140, opposite the fluid reservoir 142, and configured to collect fluid and biological particulate flowing off of the collector plate 140.

For example, the collector plate 140 can be integrated in a flexible printed circuit board, as described above. In this example, the printed circuit board can include: a set of collector plates 140 extending from a surface of the printed circuit board; and a blister reservoir 142—filled with a set volume of a hydrophobic saline solution—affixed to the surface of the printed circuit board above (e.g., vertically above) the set of collector plates 140. The printed circuit board can further include: a set of channels extending between the blister and the set of collector plates 140 along the surface of the printed circuit board and configured to direct the hydrophobic saline solution from the blister reservoir 142 (e.g., upon release from the blister reservoir) toward the set of collector plates 140; and a sample accumulator 144 arranged below (e.g., vertically below) the set of collector plates 140 and configured to capture the hydrophobic saline solution, released from the blister, including the pathogen sample.

Therefore, in this example, upon completion of a sampling period, the controller 190 can trigger the blister plunger to apply a force against the blister reservoir to pierce the blister and release the volume of the hydrophobic saline solution contained within the blister reservoir. The hydrophobic solution can then run down (e.g., via gravity) through the set of channels and over the set of collector plates 140 to extract the pathogen sample, collected during the sampling period, from the set of collector plates 140. The resulting liquid pathogen sample (e.g., the pathogen sample in the hydrophobic saline solution) can then flow downward into the trough beneath the set of collector plates 140.

Alternatively, the collector plate 140 can be configured to collect the pathogen sample directly on the surface of the collector plate 140. In this variation, the dry pathogen sample can be extracted from the surface of the collector plate 140 for post-processing and/or detection of pathogen samples remotely. In particular, in one example, a user may insert a swab (e.g., a cotton swab) into the air sampler 102 (e.g., via a door 126 arranged on the housing 120) and brush the swab across the surface of the collector plate 140 to collect the pathogen sample on the swab. The user may then store the swab in a sterile container and transport this container to a central facility (e.g., a laboratory) for detection of pathogens within the pathogen sample.

6. Variation: On-Device Pathogen Detection

In one variation, the pathogen detection system 100 can be configured to process pathogen samples for diagnostics and/or genetic sequencing directly within the air sampler 102. For example, the air sampler 102 and/or the cartridge 104 can include a genetic material load detector, a selective pathogen detector, and/or a DNA sequencer configured to detect presence and/or magnitude of a particular pathogen or pathogens.

In particular, the cartridge 104 and/or air sampler 102 can include a set of detection stages configured to receive the pathogen sample for genetic testing. In this variation, the air sampler 102 and/or the cartridge 104 can include a fluid reservoir 142 loaded with a volume of hydrophobic fluid and arranged adjacent the collector plate 140, as described above. The collector plate 140 can thus be configured to receive a preset volume (e.g., between 5 microliters and 10 microliters) of the hydrophobic fluid stored in the reservoir for extraction of a pathogen sample from the surface of the collector plate 140 as described above.

In one implementation, the cartridge 104 can include a fluid reservoir 142 loaded with hydrophobic fluid. For example, the cartridge 104 can include: a substrate 130; a collector plate 140 arranged on the substrate 130; a fluid reservoir 142 (e.g., a blister reservoir) loaded with a volume of hydrophobic fluid and arranged adjacent the collector plate 140; a sample accumulator 144 arranged on the substrate 130 adjacent the collector plate 140 and configured to collect fluid and biological particulate, forming a liquid pathogen sample, flowing off of the collector plate 140; and a manifold fluidly coupled to the sample accumulator 144 and configured to distribute fluid from the sample accumulator 144 to the detection stage. Alternatively, in another implementation, the air sampler 102 can include a fluid reservoir 142 loaded with hydrophobic fluid. In this implementation, the air sampler 102 can also include a fluid doser configured to dispense a volume of fluid onto the collector plate 140.

In this variation, the air sampler 102 and/or the cartridge 104 can further include a set of sensors 170 (e.g., biosensor, optical sensor, electrical sensor) configured to detect pathogens in a fluid pathogen sample.

In one implementation, the cartridge 104 can include a set of sensors 170 (e.g., biosensors) configured to detect pathogens in a fluid pathogen sample. The cartridge 104 can also include a databus configured to couple the set of sensors 170 to the connector 132. In this implementation, the air sampler 102 can further include a controller 190 configured to: read a set of signals from the set of sensors 170 via the databus, the connector 132, and the cartridge terminal 112; and interpret levels of biological pathogens in air flowing through the tunnel 122 based on the set of signals.

Additionally and/or alternatively, in another implementation, the air sampler 102 can include a set of sensors 170 configured to detect pathogens in a fluid pathogen sample. In this implementation, the air sampler 102 can also include: a manifold and/or set of channels configured to distribute fluid from a sample accumulator 144 and/or the collector plate 140 in the cartridge 104 to the set of sensors 170; and a controller 190 configured to read a set of signals from the set of sensors 170 and interpret levels of biological pathogens in air flowing through the tunnel 122 based on the set of signals.

Additionally and/or alternatively, in another implementation, the cartridge 104 and/or substrate 130 can include a set of (fluidic) channels and/or reaction chambers 150 loaded with a set of reagents—matched to a predefined detection assay (e.g., loop-mediated isothermal amplification) configured to enable detection of a particular pathogen in pathogen samples—and fluidly coupled to the sample accumulator 144. For example, the cartridge can include: a reaction chamber 150 configured to receive a pathogen sample collected on the collector plate and a set of reagents (e.g., lyophilized reagent beads) according to an isothermal amplification assay configured to elicit a detectable optical response (e.g., fluorescence) in fluid in the reaction chamber 150.

In the preceding implementation, the air sampler 102 further includes: an optical sensor (e.g., a fluorescence reader, a camera), arranged in the tunnel 122, facing the cartridge receptacle 110, and configured to capture an optical image of fluid in the set of reaction chambers 150 in the cartridge 104; and a controller 190 configured to interpret levels of pathogens in air flowing through the tunnel 122 based on optical signals (e.g., color changes) detected in the optical image.

6.1 Detection Stages

In this variation, the pathogen detection system 100 can include a detection module including a set of detection stages arranged within the air sampler 102 and/or the cartridge 104. For example, the pathogen detection system 100 can include: a first detection stage including a material load detector configured to detect microbe levels (e.g., presence and/or magnitude of microbes) in air drawn through the air sampler 102; a second detection stage including a selective pathogen detector configured to detect presence and/or magnitude of a particular pathogen in air drawn through the air sampler 102; and/or a third detection stage including a DNA sequencer configured to detect presence and/or magnitude of all airborne microbes (e.g., at concentrations above a minimum detectable level) in air drawn through the air sampler 102.

In one implementation, the pathogen detection system 100 can include a detection stage configured to detect anomalies in microbe levels of the external environment. In particular, the air sampler 102 and/or cartridge 104 can include a material load detector 182 (e.g., a microbe detector) configured to detect presence and/or quantity of organic (i.e., living) matter within the environment (e.g., a conference room in an office, a dining room in a restaurant) occupied by the air sampler 102 and the air sampler 102 can be configured to operate the microbe-detector at a high frequency to enable near real-time detection of changes in quantity of organic matter present in the environment in near real-time, which may be indicative of changes in microbe levels within the environment. The pathogen detection system 100 can therefore leverage these detected changes in the quantity of organic matter in the environment to predict changes in microbe levels within the area.

Additionally and/or alternatively, in another implementation, the pathogen detection system 100 can include a detection stage configured to detect presence of a particular pathogen, from a set of predefined pathogens. In particular, the detection stage can include a genetic detector—such as a biosensor and/or a set of components configured to process the pathogen sample according to a particular detection assay (e.g., an isothermal amplification assay)—configured to detect a particular predefined pathogen. Therefore, in this implementation, the pathogen detection system 100 can implement a targeted molecular diagnostic approach to interpret whether pathogens from this set of predefined pathogens are present in the environment.

Additionally and/or alternatively, in yet another implementation, the air sampler 102 can include a detection stage configured to characterize a complete pathogen profile of the pathogen sample. In this implementation, the detection stage can include a genetic sequencer 180 (e.g., a DNA and/or RNA sequencing device) configured to enable genomic sequencing of each organism (e.g., virus, bacteria, fungi) present in the pathogen sample. Therefore, in this implementation, the pathogen detection system 100 can identify each pathogen present in the pathogen sample based on the genome.

The cartridge 104 and/or air sampler 102 can be configured to include any combination of these detection stages and/or any other detection stages.

6.2 Specific Pathogen Detection

In one variation, the pathogen detection system 100 can include a detection module—including a genetic detector—configured to detect a particular set of predefined pathogens (e.g., one pathogen, five pathogens, ten pathogens), as described above.

In particular, in this variation, the air sampler 102 and/or cartridge 104 can include a set of sensors 170 configured to signal presence and/or magnitude of the set of predefined pathogens in pathogen samples collected on the collector plate 140. For example, the cartridge 104 can include: a colorimetric sensor (e.g., a fluid solution) configured to exhibit a change in color—such as via execution of a colorimetric assay—responsive to presence of a particular pathogen at the colorimetric sensor; a fluorescence sensor (e.g., a fluid solution) configured to exhibit fluorescence within a particular wavelength range and/or exhibit a change in fluorescence—such as via execution of a detection assay—responsive to presence of a particular pathogen at the fluorescence sensor; a biosensor configured to generate an electrical signal responsive to presence of a particular pathogen on the biosensor; etc.

In one implementation, the cartridge 104 can be configured to enable detection of a particular pathogen in the set of predefined pathogens. For example, a first cartridge 104 can include: a first substrate 130; a first collector plate 140; and a first pathogen sensor (e.g., colorimetric sensor, a fluorescence sensor, a biosensor, a graphene sensor)—configured to signal presence and/or magnitude of a first pathogen in a set of predefined pathogens—arranged proximal the first collector plate 140 in the first cartridge 104. Further, a second cartridge 104 can include: a second substrate 130; a second collector plate 140; and a second pathogen sensor—configured to detect presence and/or magnitude of a second pathogen in the set of predefined pathogens—arranged proximal the second collector plate 140 in the second cartridge 104. In this example, the air sampler 102 can include an optical sensor arranged proximal the cartridge receptacle 110 and configured to capture an optical image of the pathogen sensor for detection of pathogens based on signals generated by pathogen sensors. Therefore, in this example, a user may load the first cartridge 104 into the cartridge receptacle 110 of the air sampler 102 prior to a first sampling period for detection of the first pathogen in a first pathogen sample collected during the first sampling period. Later, the user may remove the first cartridge 104 from the air sampler 102 and insert the second cartridge 104 into the cartridge receptacle 110 for detection of the second pathogen in a second pathogen sample collected during the second sampling period.

Therefore, by storing these pathogen sensors—matched to a particular pathogen in the set of predefined pathogens—directly on the cartridge 104, the pathogen detection system 100 can detect different pathogens, in the set of predefined pathogens, in air in this space (e.g., containing the air sampler 102) over time based on a type of pathogen sensor installed in these cartridges 104.

Additionally and/or alternatively, in another implementation, the cartridge 104 can be configured to enable detection of a set of predefined pathogens. In particular, in this implementation, the cartridge 104 can include a set of pathogen sensors—each pathogen sensor, in the set of pathogen sensors, matched to a particular pathogen, in the set of pathogens—configured to signal presence and/or magnitude of the set of predefined pathogens. For example, the cartridge 104 can include: a substrate 130; a collector plate 140 arranged on the substrate 130; and a set of pathogen sensors fluidly coupled to the collector plate 140 (e.g., via a set of fluidic channels on the substrate 130). The air sampler 102 can include an optical sensor (e.g., an optical fluorescence reader) configured to detect presence of the set of pathogens based on fluorescence signals generated by the set of pathogen sensors. In this example, the air sampler 102 and the cartridge 104 can cooperate to: collect a pathogen sample on the collector plate 140; and distribute an aliquot of the pathogen sample to each pathogen sensor, in the set of pathogen sensors. Then, based on fluorescence emitted by each of the pathogen sensors, the pathogen detection system 100 can detect presence and/or absence of each pathogen, in the set of predefined pathogens, in this single pathogen sample.

6.2.1 Pathogen Detection: Biosensor

In one variation, the cartridge 104 can include a set of biosensors (e.g., one, ten, or 100 biosensors) arranged on the substrate 130 and configured to signal presence of a particular pathogen. For example, the substrate 130 can include a biosensor: arranged proximal and/or on the collector plate 140; defining a surface including a molecularly-imprinted polymer coating (e.g., a ZnO-based molecularly imprinted polymer coating) configured to exhibit high selectivity toward a particular pathogen; and configured to generate a detectable signal (e.g., an optical signal, an electrical signal) representing presence and/or magnitude of the particular pathogen In this variation, the pathogen detection system 100 can continuously (e.g., semi-continuously) detect presence of the particular pathogen by collecting a pathogen sample on the collector plate 140 and testing the pathogen sample on the biosensor concurrently.

In one implementation, the cartridge 104 can include a biosensor configured to signal presence of a particular pathogen in a dry pathogen sample. In this implementation, the biosensor can be arranged directly on the collector plate 140 and can be configured to continuously (e.g., once-per-second; once-per-minute, at five-minute intervals) sense for presence of the particular pathogen in a dry pathogen sample during and/or after collection of the dry pathogen sample on the collector plate 140.

For example, the cartridge 104 can include: a printed circuit board; a collector plate 140 (e.g., a conductive electrode surface) arranged on the printed circuit board; and a biosensor including a ZnO-based molecularly-imprinted polymer coating applied to a surface of the collector plate 140 and configured to generate a detectable signal (e.g., an optical signal, an electrochemical signal, an electrical signal) responsive to presence of a particular pathogen, in a set of pathogens, on the surface of the collector plate 140. In particular, the ZnO-based molecularly-imprinted polymer coating can be configured to exhibit high affinity for viral proteins corresponding to the particular pathogen. In this example, the air sampler 102 can include a controller 190 configured to read the detectable signal—such as from the biosensor (e.g., via a databus coupling the biosensor to the cartridge receptacle 110) and/or from an image captured by an optical sensor of the biosensor—and interpret levels of the particular pathogen in air flowing through the tunnel 122 based on the electrical signal.

In another implementation, the cartridge 104 can include a biosensor configured to signal presence of a particular pathogen in a fluid (e.g., liquid) pathogen sample. In this implementation, the air sampler 102 and/or cartridge 104 can include a fluid reservoir 142 filled with a volume of hydrophobic fluid (e.g., a buffer solution) configured to supply hydrophobic fluid to the collector plate 140 to enable sensing by the biosensor.

In one example, the cartridge 104 can include a biosensor arranged directly on the collector plate 140. In particular, in this example, the cartridge 104 can include: a substrate 130 (e.g., a printed circuit board); a collector plate 140 (e.g., a conductive electrode surface) arranged on the substrate 130; and a biosensor including a polymer coating (e.g., a ZnO-based molecularly-imprinted polymer coating) applied to a surface—such as a superhydrophobic-coated electrode surface—of the collector plate 140 and configured to generate a signal (e.g., an electrical signal, a colorimetric signal, a fluorescence signal) responsive to presence of a particular pathogen, in a set of pathogens, on the surface of the collector plate 140. Further, in this example, the air sampler 102 can include: a fluid reservoir 142 loaded with a volume of hydrophobic fluid and arranged proximal the collector plate 140; a fluid doser configured to dispense metered volumes of hydrophobic fluid from the reservoir and onto the collector plate 140; and a controller 190 configured to read the signal generated by the biosensor and interpret presence of the particular pathogen based on the signal. Alternatively, the cartridge 104 can include a fluid reservoir 142 (e.g., a blister reservoir) preloaded with a volume of hydrophobic fluid for dispensation onto the collector plate 140.

In this example, the air sampler 102 and the cartridge 104 can cooperate to collect a pathogen sample on the collector plate 140 during a sampling period. Then, in response to expiration of the sampling period, the air sampler 102 can dispense a metered volume of the hydrophobic fluid from the reservoir onto the collector plate 140 including the biosensor integrated into the surface. Then, in response to dispensing the metered volume onto the collector plate 140 (e.g., within 30 seconds, 1 minute, or 5 minutes), the controller 190 can read the signal generated by the biosensor—responsive to contact with the fluid pathogen sample—to interpret presence of the particular pathogen in this pathogen sample. If no signal is detected by the controller 190, the controller 190 can interpret absence of the particular pathogen in the pathogen sample.

Further, in the preceding example, the cartridge 104 can include multiple collector plates 140 (e.g., an array of collector plates 140) arranged on the substrate 130, each collector plate 140 including a biosensor that is configured to generate a detectable signal responsive to detecting a particular pathogen, in the set of pathogens, at the biosensor.

Alternatively, in another example, the cartridge 104 can include a biosensor arranged on the substrate 130 and coupled to the collector plate 140. In this example, the cartridge 104 can include: a substrate 130 (e.g., a printed circuit board); a collector plate 140 (e.g., a superhydrophobic-coated electrode surface) arranged on the substrate 130; and a biosensor including a polymer coating (e.g., a ZnO-based molecularly-imprinted polymer coating) applied to a surface of the substrate 130 and configured to generate a signal (e.g., an electrical signal, a colorimetric signal, a fluorescence signal) responsive to presence of a particular pathogen, in a set of pathogens, on the biosensor; and a fluid reservoir 142 fluidly coupled to the collector plate 140 and loaded with a volume of hydrophobic fluid configured to be dispensed onto the collector plate 140. Further, in this example, the air sampler 102 can include a controller 190 configured to read the signal generated by the biosensor and interpret presence of the particular pathogen based on the signal.

In this example, the air sampler 102 and the cartridge 104 can cooperate to: collect a pathogen sample on the collector plate 140 during a sampling period; periodically (e.g., once-per-minute, at 10-minute intervals, once-per-hour) dispense metered volumes of hydrophobic fluid from the reservoir onto the collector plate 140—such as via a first channel, in a set of microfluidic channels, configured to direct fluid from the reservoir over the surface of the collector plate 140—to generate a fluid pathogen sample; and collect the fluid pathogen sample on the biosensor—such as via a second channel, in the set of microfluidic channels, configured to direct fluid from the collector plate 140 onto the biosensor. The controller 190 can then interpret presence (and/or absence) of the particular pathogen in this fluid pathogen sample based on signals generated by the biosensor. Therefore, in this example, by separating the biosensor from the collector plate 140 and thereby transferring fluid off of the collector plate 140, the pathogen detection system 100 can continue sampling onto the collector plate 140 during transfer of the fluid pathogen sample toward the biosensor and/or during sensing of the fluid pathogen sample by the biosensor.

Additionally, in the preceding example, the cartridge 104 can include multiple biosensors configured to signal presence of a set of pathogens. For example, the cartridge 104 can include: a substrate 130 including a set of microfluidic channels; a collector plate 140 arranged on the substrate 130; an array of biosensors arranged on the substrate 130, each biosensor in the array of biosensors configured to signal detection of a particular pathogen, in the set of pathogens, and fluidly coupled to the collector plate 140 via a microfluidic channel in the set of microfluidic channels; and a fluid reservoir 142 prefilled with a volume of hydrophobic fluid (e.g., a buffer solution). The cartridge 104 can therefore be configured to: collect a single pathogen sample on the collector plate 140; and distribute aliquots of this pathogen sample—mixed with a metered volume of the hydrophobic fluid—via the set of microfluidic channels to each biosensor (or a subset of biosensors) in the array of biosensors, thereby enabling detection of each pathogen, in the set of pathogens during a single sampling period.

Additionally and/or alternatively, in the preceding example, the cartridge 104 can include multiple biosensors configured to signal presence of a particular pathogen and configured to be activated (e.g., by the controller 190) during different sampling periods.

6.2.2 Pathogen Detection: Detection Assay

In one variation, the cartridge 104 can include a detection module configured to execute a particular detection assay (e.g., an isothermal amplification assay) to detect a particular pathogen in the pathogen sample. In this variation, the cartridge 104 can include a set of reaction chambers 150 (e.g., one, ten, or 100 reaction chambers 150) arranged on the substrate 130 and configured to enable execution of a particular detection assay—such as via mixing of a pathogen sample with a particular set of reagents according to a particular set of reaction conditions (e.g., temperature, pressure, duration)—corresponding to the particular pathogen. For example, the reaction chamber 150 can be configured to: receive a pathogen sample; receive a reaction solution—such as including a reaction buffer and/or reconstituted lyophilized reagent beads—configured to interact (e.g., bind) with a particular pathogen (e.g., with viral proteins of the particular pathogen) in the set of pathogens; and hold a (liquid) bioaerosol mixture—including the pathogen sample mixed with the reaction solution—under a particular set of reaction conditions in order to enable generation of a detectable signal (e.g., an optical signal) responsive to presence of the particular pathogen in the reaction solution.

In this variation, the reaction chamber 150 can be configured to hold the pathogen sample, mixed with the set of reagents, under a particular set of conditions to enable execution of the detection assay (e.g., a DNA or RNA isothermal amplification assay). In particular, the detection assay can be configured to: amplify a target sequence (e.g., a target DNA sequence) corresponding to a particular pathogen; and elicit expression of an optical signal (e.g., a fluorescence signal)—in the reaction solution—representative of magnitude and/or presence of the particular pathogen in the reaction solution. Therefore, the reaction chamber 150 can be configured to receive the pathogen sample and the set of reagents in a particular order and according to the particular set of conditions defined by the DNA-amplification reaction in order to enable amplification of the target sequence.

For example, the reaction chamber 150 can be configured to enable execution of a loop-mediated isothermal amplification (or "LAMP") reaction configured to generate a detectable signal during execution of the reaction responsive to presence of the particular pathogen in the reaction solution (e.g., including a pathogen sample mixed with a set of reagents). Alternatively, in another example, the reaction chamber 150 can be configured to enable execution of a cDNA-mediated reaction—including annealing, selection, extension, and ligation of the target sequence—configured to generate a detectable signal during execution of the reaction responsive to presence of the particular pathogen in the reaction solution.

For example, the pathogen detection system 100 can be configured to detect a particular pathogen, in a set of predefined pathogens, via a DNA-amplification reaction (e.g., loop-mediated isothermal amplification reaction or "LAMP" reaction, DASL reaction). In this example, the cartridge 104 can include: a substrate 130; a collector plate 140 arranged on the substrate 130 and configured to collect a pathogen sample; and a reaction chamber 150 configured to receive a pathogen sample (e.g., charged bioaerosols extracted from air flowing through the tunnel 122 of the air sampler 102) for execution of the LAMP reaction within the reaction chamber 150; a set of heating elements 154 arranged proximal (e.g., around) the reaction chamber 150 and configured to hold the reaction chamber 150 at a set temperature for the LAMP reaction; and a set of fluidic channels and/or reservoirs fluidly coupled to the reaction chamber 150 and containing a set of reagents (e.g., reaction buffer, reconstituted reagent beads, fluid reagents) configured to form a reaction solution corresponding to the particular pathogen and the LAMP reaction.

When combined and/or held in the reaction chamber 150 (e.g., at the set temperature)—such as succeeding expiration of a sampling period—the reaction solution and the pathogen sample can form a (liquid) bioaerosol mixture configured to generate an optical signal (e.g., fluorescence signal, colorimetric signal) responsive to presence of the particular pathogen in the bioaerosol mixture.

Additionally and/or alternatively, the cartridge 104 and/or air sampler 102 can include an optical sensor arranged within and/or adjacent the reaction chamber 150 and configured to capture and/or detect the optical signal indicative of pathogen presence in the pathogen sample. For example, the air sampler 102 and/or cartridge 104 can include: a fluorescence reader configured to capture a spectral image (e.g., in the electromagnetic spectrum) of the pathogen sample to measure fluorescence of the pathogen sample; a camera configured to capture a color image of the pathogen sample; and/or colorimetric test strip configured to exhibit a particular color change—when contacting the pathogen sample—responsive to presence of the particular pathogen in the pathogen sample. Further, the air sampler 102 can include the controller 190 configured to interpret presence of the particular pathogen in the pathogen sample based on the set of optical signals.

6.2.2.1 Reaction Chamber & Collector Plate

In one implementation, the cartridge 104 can include a reaction chamber 150 preloaded with the collector plate 140, such that the pathogen sample is collected directly within the reaction chamber 150 on the collector plate 140. In this implementation, by arranging the collector plate 140 within the reaction vessel—such as forming a bottom, interior surface of the reaction vessel—the pathogen detection system 100 can confine collection of the pathogen sample and detection of pathogens in this pathogen sample to a single region on the substrate 130 within the cartridge 104, thereby reducing complexity of the substrate 130 and reducing time to detection by eliminating transfer of the pathogen sample to the reaction chamber 150.

For example, the cartridge 104 can include: a substrate 130; a collector plate 140 arranged on the substrate 130 and configured to collect a pathogen sample during a sampling period; a reaction chamber 150 configured to receive the pathogen sample and a set of reagents for detection of pathogens via the LAMP reaction during a detection period succeeding the sampling period; and a set of reagent reservoirs 152 configured to release the set of reagents into the reaction chamber 150 during the detection period. In this example, the cartridge 104 and/or air sampler 102 can include: a set of heating elements 154 configured to heat and/or cool the set of reagents, the pathogen sample, and/or the reaction chamber 150; and a set of sensors 170 (e.g., reagents, optical sensors, electrical sensors) configured to detect pathogens in the pathogen sample. The air sampler 102 can also include a controller 190 configured to read a set of signals from the set of sensors 170 and interpret levels of biological pathogens in air flowing through the tunnel 122 based on the set of signals.

In particular, in this example, the collector plate 140 can be configured to form a bottom surface of the reaction chamber 150, such that the pathogen sample is collected at the bottom surface of the reaction chamber 150 during the sampling period. The set of reagent reservoirs 152 (e.g., a set of blisters) can be arranged within the reaction chamber 150, such as affixed to the side walls of the reaction chamber 150, vertically above the collector plate 140 within the cartridge 104. Alternatively, the set of reagent reservoirs 152 can be affixed to a lid (e.g., an upper surface) of the reaction chamber 150 that is configured to: open during the sampling period to enable collection of the pathogen sample on the collector plate 140; and close during the detection period to seal the reaction chamber 150 during the LAMP reaction. Then, during the detection period, succeeding the sampling period, the set of reagents can be released from the set of reagent reservoirs 152 in a particular time-based sequence according to the LAMP reaction.

The set of heating elements 154 can be arranged in the air sampler 102 about the reaction chamber 150 and configured to heat the reaction chamber 150 to a set temperature to trigger initiation of the LAMP reaction. The set of heating elements 154 can also be configured to maintain a temperature within the reaction chamber 150 and/or cool the reaction chamber 150 during the detection period. These heating elements 154 can be decoupled from the reaction chamber 150, such that when the reaction chamber 150 is replaced prior to a next sampling period, the heating elements 154 remain within the air sampler 102 and can be reused over multiple detection periods.

The set of sensors 170 can be configured to detect results of the LAMP reaction. In particular, in this example, the set of sensors 170 can include an optical sensor configured to detect a color of the liquid pathogen sample after completion of the LAMP reaction, which may indicate presence of a particular pathogen. Additionally and/or alternatively, the set of sensors 170 can include an optical sensor configured to detect fluorescence (e.g., presence and/or intensity) of the liquid pathogen sample. Additionally and/or alternatively, the set of sensors 170 can include an electrical sensor configured to detect changes in lateral flow of the liquid pathogen sample.

In this example, the set of sensors 170 can be fixed within the detection module of the air sampler 102 and thereby decoupled from the replaceable reaction chamber 150.

6.2.1.2 Microfluidic Disk

In another implementation, the cartridge 104 can include a set of reaction chambers 150 fluidly coupled to a set of collector plates 140 and arranged on a rotatable substrate (e.g., a disk) configured to rotate between sampling periods to load new (clean) reaction chambers 150 in preparation for a next sampling period.

In particular, in this implementation, the cartridge 104 can include: a printed circuit board including a set of microfluidic channels integrated into the substrate 130; a set of collector plates 140 arranged on the substrate 130; a set of reagent reservoirs 152 coupled to the substrate 130 and containing a set of reagents matched to a particular detection assay; and a disk coupled to the printed circuit board and defining an array of reaction microwells (i.e., the set of reaction chambers 150) fluidly coupled to the set of collector plates 140 and the set of reagent reservoirs 152 via the set of microfluidic channels. The printed circuit board can also include a local controller 190 configured to selectively route fluid (e.g., a reconstituted pathogen sample, the set of reagents) to the array of reaction microwells for processing and detection of pathogens.

For example, during a first sampling period, the air sampler 102 and the cartridge 104 can cooperate to collect a first pathogen sample on a first collector plate 140, in a set of collector plates 140, arranged on the printed circuit board. In response to expiration of the first sampling period, the local controller 190 can trigger transfer of a buffer solution from a first reservoir arranged on the printed circuit board and over the collector plate 140 to capture the pathogen sample via a first microfluidic channel in the set of microfluidic channels integrated into the printed circuit board. The local controller 190 can then route the liquid pathogen sample, in the buffer solution, toward a first reaction microwell—in an array of reaction microwells arranged on a rotating disk coupled to the printed circuit board—according to a first pathway configured to mix the liquid pathogen sample with additional reagents in the set of reagents. Finally, the microvolume of the liquid pathogen sample—including the buffer solution and additional reagents—can be processed in the first reaction microwell according to a particular detection assay (e.g., the DASL reaction, the LAMP reaction). In response to completion of the particular detection assay, an optical sensor—such as a fluorescence reader—can record an image of the liquid pathogen sample in the first reaction microwell to capture a set of signals representing presence of a particular pathogen, in a set of pathogens, in the liquid pathogen sample. The pathogen detection system 100 can then interpret presence of the particular pathogen in this pathogen sample based on the set of signals (e.g., based on fluorescence).

In this example, prior to a second sampling period succeeding the first sampling period, the rotating disk coupled to the printed circuit board can be rotated to displace the first (dirty) reaction microwell and load a second (clean) reaction microwell. The pathogen detection system 100 can then continue to load a new reaction microwell for each successive sampling period.

Therefore, by enabling processing of microvolumes of liquid pathogen samples in microwells, the pathogen detection system 100 can enable an increased quantity of reaction chambers 150 within the cartridge 104, thereby extending a duration between cartridge 104 replacement and/or increasing granularity of pathogen detection by enabling increasing frequency of pathogen collection. Further, by storing, transporting, and reacting fluids (e.g., reagents, buffer solutions, pathogen sample) in microchannels and/or microwells—and therefore increasing a surface area-to-volume ratio—the pathogen detection system 100 can reduce a duration required to heat and/or cool these fluids, thereby reducing time to detection of pathogens in pathogen samples.

7. On-Site Detection: Mobile Cartridge Reader

In one variation, the pathogen detection system 100 can include a mobile, detection kit (or "cartridge reader") configured to receive the cartridge 104 from the air sampler 102 for processing of the pathogen sample collected on the collector plate 140.

The cartridge 104 reader can be configured to process pathogen samples at a particular rate (e.g., 50 samples per day, 100 samples per day, 200 samples per day) such that the pathogen detection system 100 can track and/or report detected pathogens and/or pathogen levels across numerous spaces (e.g., regions, rooms, floors) within a facility and at multiple timepoints throughout a single day, thereby enabling semi-continuous, (near) real-time pathogen detection throughout a facility.

Additionally, in this variation, the pathogen detection system 100 can be configured to instruct a user or users at the facility to load the cartridge 104 reader with a particular cartridge 104 to initiate a processing cycle for a pathogen sample collected in the particular cartridge 104.

For example, the pathogen detection system 100 can trigger collection of a first pathogen sample onto a first collector plate 140 from a first cartridge 104 loaded in the air sampler 102 during a first sampling period. Then, in response to expiration of the first sampling period, the pathogen detection system 100 can alert a user (e.g., via a native application executing on the user's computing device, via a blinking light arranged on the housing 120 of the air sampler 102) to transfer the first cartridge 104—containing the first collector plate 140—from the air sampler 102 to the cartridge 104 reader. In particular, the user may: eject the first collector plate 140 (and substrate 130) from the cartridge receptacle 110 and back into the first cartridge 104; deliver the cartridge 104 to a designated location within the facility containing the cartridge 104 reader; and eject the first collector plate 140 into the cartridge 104 reader for further processing without any contact between the user and the first pathogen sample. Further, the user may insert a second cartridge 104 into the cartridge receptacle 110 of the air sampler 102 to load a second (clean) collector plate 140 in the tunnel 122 in preparation for second sampling period.

Alternatively, the air sampler 102 can be configured to collect and store a pathogen sample for further processing at a remote location (e.g., at a laboratory). For example, the air sampler 102 and/or controller 190 can trigger initiation of a sampling period by actuating the power supply 160 of the air sampler 102. Then, upon completion of the sampling period and/or subsequent detection periods, the user may eject the substrate 130 and collector plate 140 from the cartridge receptacle 110 and back into the cartridge 104, such as by again engaging (e.g., clicking) the eject button. The user may then deliver the cartridge 104—containing the dirty collector plate 140—to a designated location for further processing and/or proper disposal without any contact (e.g., physical contact of surfaces or airborne contact) between the user and the collected pathogen sample.

The systems and methods described herein can be embodied and/or implemented at least in part as a machine configured to receive a computer-readable medium storing computer-readable instructions. The instructions can be executed by computer-executable components integrated with the application, applet, host, server, network, website, communication service, communication interface, hardware/firmware/software elements of a user computer or mobile device, wristband, smartphone, or any suitable combination thereof. Other systems and methods of the embodiment can be embodied and/or implemented at least in part as a machine configured to receive a computer-readable medium storing computer-readable instructions. The instructions can be executed by computer-executable components integrated by computer-executable components integrated with apparatuses and networks of the type described above. The computer-readable medium can be stored on any suitable computer readable media such as RAMs, ROMs, flash memory, EEPROMs, optical devices (CD or DVD), hard drives, floppy drives, or any suitable device. The computer-executable component can be a processor but any suitable dedicated hardware device can (alternatively or additionally) execute the instructions.

As a person skilled in the art will recognize from the previous detailed description and from the figures and claims, modifications and changes can be made to the embodiments of the invention without departing from the scope of this invention as defined in the following claims.

The invention claimed is:

1. A system comprising:

an air sampler comprising:

a housing defining an inlet and an outlet;

a tunnel extending between the inlet and the outlet within the housing;

a charge electrode arranged within the tunnel proximal the inlet;

a cartridge receptacle arranged within the housing, proximal the outlet, and comprising a cartridge terminal; and a power supply configured to drive a voltage between the charge electrode and the cartridge terminal to generate an electric field within the tunnel and charge bioaerosols in air flowing through the tunnel; and a replaceable cartridge comprising:

a substrate;

a collector plate arranged on the substrate and configured to attract charged bioaerosols moving through the tunnel onto a surface of the collector plate; and an electrical connector configured to transiently engage the cartridge receptacle to locate the substrate and the collector plate within the tunnel and electrically couple the collector plate to the cartridge terminal.

2. The system of claim 1, wherein the air sampler is configured to:

ingest a stream of ambient air from an external environment containing the air sampler through the inlet of the tunnel; and cooperate with the replaceable cartridge to collect a pathogen sample comprising charged bioaerosols extracted from the stream of ambient air on the collector plate for detection of a set of pathogens in the pathogen sample.

3. The system of claim 1:

wherein the replaceable cartridge comprises a set of sensors configured to signal presence of a set of pathogens in a pathogen sample comprising charged bioaerosols collected on the collector plate; and wherein the air sampler further comprises a controller configured to:

read a set of signals from the set of sensors; and interpret presence of the of the set of pathogens in air flowing through the tunnel based on the set of signals.

4. The system of claim 3:

wherein the replaceable cartridge further comprises a reservoir containing a volume of a hydrophobic fluid and configured to periodically release a metered volume of the hydrophobic fluid onto the collector plate; and wherein the set of sensors comprises a set of biosensors, each biosensor in the set of biosensors:

fluidly coupled to the collector plate;

configured to receive a fluid aliquot of the pathogen sample from the collector plate; and configured to generate a signal, in the set of signals, representing presence of a particular pathogen in the set of pathogens.

5. The system of claim 3, wherein the set of sensors comprises:

a first sensor configured to detect presence of a first pathogen, in the set of pathogens, in the pathogen sample; and a second sensor configured to detect presence of a second pathogen, in the set of pathogens, in the pathogen sample.

6. The system of claim 1:

wherein the substrate comprises a printed circuit board comprising a set of traces integrated into the printed circuit board;

wherein the collector plate is arranged on the printed circuit board and comprises a conductive surface configured to collect charged bioaerosols in air flowing through the tunnel; and wherein the electrical connector is configured to transiently engage the cartridge receptacle to electrically couple the collector plate to the cartridge terminal via a first trace, in the set of traces, extending between the electrical connector and the collector plate.

7. The system of claim 6:

wherein the replaceable cartridge comprises a second collector plate arranged on the printed circuit board; and wherein the electrical connector is configured to transiently engage the cartridge receptacle to:

electrically couple the collector plate to the cartridge terminal via the first trace; and electrically couple the second collector plate to the cartridge terminal via a second trace, in the set of traces, extending between the electrical connector and the second collector plate.

8. The system of claim 1:

wherein the replaceable cartridge comprises:

a reaction chamber fluidly coupled to the collector plate;

a set of reagent reservoirs:

loaded with a set of reagents corresponding to a defined detection assay; and configured to release reagents, in the set of reagents, into the reaction chamber according to the defined detection assay; and a set of heating elements configured to regulate a temperature of the reaction chamber according to the defined detection assay; and wherein the air sampler comprises an optical sensor:

arranged in the tunnel; and configured to record a set of optical signals generated by fluid in the reaction chamber responsive to execution of the defined detection assay, the set of optical signals representative of presence of a set of pathogens in fluid within the reaction chamber.

9. The system of claim 8:

wherein the collector plate is arranged on the substrate and within the reaction chamber; and wherein the set of reagent reservoirs is arranged within the reaction chamber and comprises a set of pierceable membranes preloaded with the set of reagents.

10. The system of claim 8:

wherein the set of reagent reservoirs is loaded with the set of reagents:

corresponding to the defined detection assay comprising an isothermal amplification assay;

comprising a reaction buffer and a set of lyophilized reagent beads associated with the isothermal amplification assay; and configured to react with a pathogen sample comprising charged bioaerosols collected on the collector plate to generate a set of fluorescence signals representing presence of the set of pathogens;

wherein the optical sensor is configured to record the set of fluorescence signals generated in the reaction chamber responsive to execution of the isothermal amplification assay; and further comprising a controller configured to:

read the set of fluorescence signals from the optical sensor; and interpret presence of the set of pathogens in the pathogen sample based on the set of fluorescence signals.

11. The system of claim 1:

further comprising a second replaceable cartridge comprising:

a second substrate;

a second collector plate arranged on the second substrate and configured to collect charged bioaerosols moving through the tunnel; and a second electrical connector configured to transiently engage the cartridge receptacle to locate the second substrate and the second collector plate within the tunnel and electrically couple the second collector plate to the cartridge terminal;

wherein the housing defines an opening arranged proximal the cartridge terminal; and wherein the air sampler is configured to:

receive the replaceable cartridge, via the opening, within the cartridge receptacle for collection of a first pathogen sample on the collector plate during a first sampling period; and receive the second replaceable cartridge, via the opening, in replacement of the replaceable cartridge, within the cartridge receptacle for collection of a second pathogen sample during a second sampling period succeeding the first sampling period.

12. The system of claim 1, further comprising a cleaning module configured to sanitize surfaces of the air sampler between sampling periods to prevent sample contamination.

13. A system comprising:

an air sampler comprising:

a housing defining an inlet and an outlet;

a tunnel extending between the inlet and the outlet within the housing;

a set of charging elements arranged within the tunnel proximal the inlet;

a cartridge receptacle arranged proximal the outlet and comprising a cartridge terminal; and a power supply configured to drive a voltage between the set of charging elements and the cartridge terminal; and a replaceable cartridge comprising:

a substrate;

a set of collector plates arranged on the substrate, each collector plate, in the set of collector plates, configured to collect pathogen samples of charged bioaerosols moving through the tunnel;

an electrical connector configured to transiently engage the cartridge receptacle to locate the substrate within the tunnel and electrically couple the set of collector plates to the cartridge terminal; and a set of sensors configured to generate a set of signals representing presence of a set of pathogens in pathogen samples collected on the set of collector plates; and a controller configured to interpret presence of the set of pathogens in air flowing through the tunnel based on the set of signals.

14. The system of claim 13:

wherein the set of collector plates comprises a first collector plate and a second collector plate; and wherein the controller is configured to:

during a first sampling period, trigger electrical coupling of the cartridge terminal to the first collector plate to activate the first collector plate for collection of a first pathogen sample on the first collector plate; and during a second sampling period succeeding the first sampling period, trigger electrical coupling of the cartridge terminal to the second collector plate to activate the second collector plate for collection of a second pathogen sample on the second collector plate.

15. The system of claim 13:

wherein the set of collector plates comprises:

a first collector plate configured to collect a first pathogen sample during a first sampling period for detection of a first pathogen in the set of pathogens; and a second collector plate configured to collect a second pathogen sample during the first sampling period for detection of a second pathogen in the set of pathogens; and wherein the set of sensors comprises:

a first sensor configured to detect presence of the first pathogen and generate a first signal, in the set of signals, representing presence of the first pathogen; and a second sensor configured to detect presence of the second pathogen and generate a second signal, in the set of signals, representing presence of the second pathogen.

16. The system of claim 13:

wherein the replaceable cartridge further comprises a fluid reservoir preloaded with a volume of fluid and fluidly coupled to the set of collector plates;

wherein the set of sensors comprises a set of biosensors, each biosensor, in the set of biosensors:

arranged on a collector plate in the set of collector plates; and configured to generate a signal, in the set of signals, representing presence of a particular pathogen, in the set of pathogens, in fluid contacting the biosensor; and wherein the controller is configured to interpret presence of the set of pathogens in air flowing through the tunnel based on the set of signals generated by the set of biosensors.

17. The system of claim 13:

wherein the replaceable cartridge comprises:

a set of reagent reservoirs coupled to the substrate and containing a set of reagents corresponding to a detection assay;

an array of reaction microwells fluidly coupled to the set of collector plates and the set of reagent reservoirs; and a set of microfluidic channels configured to transport fluid to the set of reaction microwells; and wherein the set of sensors comprises an optical sensor arranged proximal the array of reaction microwells and configured to read an optical signal from fluid in the array of reaction microwells for interpreting presence of a particular pathogen, in the set of pathogens.

18. The system of claim 17, wherein the air sampler further includes:

a genetic material load detector arranged in the tunnel and configured to detect presence of organic matter in air flowing through the tunnel; and a genetic sequencer configured to receive pathogen samples from the set of collector plates to detect presence of the set of pathogens in pathogen samples collected on the set of collector plates.

19. A system comprising:

an air sampler comprising:

a housing defining an inlet and an outlet;

a tunnel extending between the inlet and the outlet within the housing;

a set of charging elements arranged within the tunnel proximal the inlet;

a cartridge receptacle arranged proximal the outlet and comprising a cartridge terminal; and a power supply configured to drive a voltage between the set of charging elements and the cartridge terminal;

a first replaceable cartridge configured to transiently couple to the air sampler during a first sampling period and comprising:

a first substrate;

a first collector plate arranged on the first substrate and configured to attract charged bioaerosols, moving through the tunnel, onto a surface of the first collector plate to collect a first pathogen sample during the first sampling period;

a first electrical connector configured to transiently engage the cartridge receptacle to locate the first substrate within the tunnel and electrically couple the first collector plate to the cartridge terminal; and a first sensor configured to generate a first signal representing presence of a first set of pathogens in the first pathogen sample; and a second replaceable cartridge configured to transiently couple to the air sampler during a second sampling period, distinct from the first sampling period, and comprising:

a second substrate;

a second collector plate arranged on the second substrate and configured to attract charged bioaerosols, moving through the tunnel, onto a surface of the second collector plate to collect a second pathogen sample during the second sampling period;

a second electrical connector configured to transiently engage the cartridge receptacle to locate the second substrate within the tunnel and electrically couple the second collector plate to the cartridge terminal; and a second sensor configured to generate a second signal representing presence of a second set of pathogens in the second pathogen sample.

20. The system of claim 19, further comprising a controller configured to:

based on the first signal, interpret presence of each pathogen, in the first set of pathogens, in air flowing through the tunnel during the first sampling period; and based on the second signal, interpret presence of each pathogen, in the second set of pathogens, in air flowing through the tunnel during the second sampling period.

* * * * *